United States Patent [19]

Spry

[11] 3,953,436
[45] Apr. 27, 1976

[54] 3,4-DICARBOXYCEPHALOSPORINS AND DERIVATIVES

[75] Inventor: Douglas O. Spry, Indianapolis, Ind.

[73] Assignee: Eli Lilly and Company, Indianapolis, Ind.

[22] Filed: Apr. 19, 1974

[21] Appl. No.: 462,459

[52] U.S. Cl. .............................. 260/243 C; 424/246
[51] Int. Cl.² .............. C07D 501/18; C07D 501/24; C07D 501/60
[58] Field of Search ................................. 260/243 C

[56] References Cited
UNITED STATES PATENTS 3,864,338  8/1970  Bohme et al. .................... 260/243 C
3,872,086  3/1975  Barton et al. .................... 260/243 C Primary Examiner—Nicholas S. Rizzo
Assistant Examiner—Mary C. Vaughn
Attorney, Agent, or Firm—Steven R. Lammert; Walter E. Buting; Everet F. Smith

[57] ABSTRACT

7-Acylamino and 7-amino-3-carboxy-3-cephem-4-carboxylic acids and derivatives thereof, which are useful as antibiotics or as intermediates in preparing antibiotic substances, are prepared by an NBS oxidation of acetal derivatives of 3-formyl cephalosporins.

31 Claims, No Drawings

3,4-DICARBOXYCEPHALOSPORINS AND DERIVATIVES

BACKGROUND OF THE INVENTION

This invention relates to the cephalosporin class of antibiotics. In particular, this invention relates to certain of such cephalosporins having in the 3-position a carboxy group or a functionality derived from said carboxy group. Such functional groups include an ester, thioester, amide, or other like groups prepared by reacting a mixed anhydride derivative or acid halide of the 3-carboxy group with the appropriate nucleophilic reagent. The compounds of this invention are therapeutically useful antibiotic compounds or intermediates useful in the preparation of such antibiotics.

Previously, numerous antibiotics of the cephalosporin class have been described. These antibiotics, all possessing the same basic ring structure comprising the 4-membered β-lactam ring fused to a 6-membered dihydrothiazine ring, differ from one another structurally and biologically in many respects. Structurally, the known cephalosporin antibiotics differ in the nature of the 7-acylamido substituent and also in the nature of the substituent in the 3-position of the dihydrothiazine ring. The desacetoxycephalosporanic acids, for example, cephalexin, have a 3-methyl substituent. Numerous cephalosporins having a substituted methyl group in the 3-position have also been described. The desacetylcephalosporins have a 3-hydroxymethyl substituent. The 3-alkylthiomethyl and 3-heteroarylthiomethyl cephalosporins have also been described. More recently, certain 3-methoxymethylcephalosporins were disclosed in U.S. Pat. No. 3,665,003 and 3-bromomethylcephalosporins were disclosed in U.S. Pat. Nos. 3,647,788, 3,668,203 and 3,637,678.

In addition to the 3-methyl or 3-substituted methyl cephalosporins, 3-formyl substituted cephalosporins have also been disclosed. In U.S. Pat. No. 3,351,596, issued Nov. 7, 1967, Chamberlin claimed a process comprising reacting a 3-hydroxymethyl-7-acylamino-3-cephem-4-carboxylic acid compound with a diazo compound to obtain a 3-formylcephalosporin ester and then reacting that ester with an oxidizing agent selected from the group consisting of manganese dioxide and chromium trioxide. A similar conversion was described in Belgium Pat. No. 768,653. The corresponding 3-formylcephalosporin sulfoxides were disclosed in U.S. Pat. No. 3,674,784.

Another class of cephalosporins differing in the nature of the substituent at the 3-position was described in Netherlands Pat. No. 7,206,931, wherein certain 3-unsubstituted cephalosporins, as well as a method for their preparation by decarbonylation of the corresponding 4-formyl compounds.

It is an object of this invention to provide new cephalosporin compounds which are useful as antibiotics or as intermediates in processes for preparing antibiotics.

It is another but more specific object of this invention to provide new structurally unique compounds of the cephalosporin class, wherein a carboxy group or a derivative thereof is attached directly to the carbon in the 3-position of the dihydrothiazine ring.

SUMMARY OF THE INVENTION

This invention is directed to cephalosporin compounds having a carboxy group, or a first order derivative thereof, at the C-3 position on the dihydrothiazine ring of the cephem ring system. The 7-acylamino and 7-amino-3-carboxycephem compounds and their derivatives provided by this invention are prepared by oxidizing an acyclic or cyclic acetal derivative of a 7-acylamino-3-formylcephem-4-carboxylic acid ester compound with N-bromo-succinimide to give an intermediate 7-acylamino-3-[alkoxycarbonyl or 2-bromoalkoxycarbonyl]cephem derivative. The latter type compound is subsequently deesterified to give the corresponding 3-carboxylic acid compound. First order derivatives of the 3-carboxy group, comprising esters, thioesters, amides, acylazides and the like groups are prepared by reacting an acid chloride or mixed anhydride derivative of a cephem 3-carboxylic acid compound with the appropriate nucleophilic reagent. Removal of the C-4 ester protecting group gives the novel active antibiotic substances provided by this invention, which compounds can be employed to combat infections caused by gram-positive and gram-negative microorganisms.

DETAILED DESCRIPTION OF THE INVENTION

The cephalosporin compounds of this invention are represented by the following Formula I

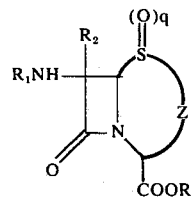

wherein Z is a group of the formula

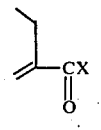

or

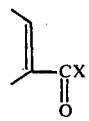

wherein X is (a) azido, chloro, bromo, or $C_2$-$C_5$ alkylcarbonyldioxy; or b. a group of the formula —$OR_3$ wherein $R_3$ is hydrogen, $C_1$-$C_6$ alkyl, $C_2$-$C_6$ haloalkyl, 2,2,2-trihaloethyl, methoxybenzyl, nitrobenzyl, benzyl, diphenylmethyl, $C_2$-$C_5$ alkanoyloxymethyl, phenyl or a pharmaceutically acceptable nontoxic cation; or c. a group of the formula —$SR_4$ wherein $R_4$ is $C_1$-$C_6$ alkyl, phenyl, benzyl, 1-methyl-1,2,3,4-tetrazol-5-yl or 1,3,4-thiadiazol-2-yl; or d. a group of the formula

wherein $R_5$ is hydrogen, $C_1$-$C_6$ alkyl, benzyl, phenyl, or tolyl and Q is hydrogen, $C_1$-$C_6$ alkyl, benzyl, $C_1$-$C_7$ alkoxy, hydroxy, amino, anilino, guanyl, or $C_1$-$C_3$ acylamino with the limitation that when Q is guanyl or $C_1$-$C_3$ acylamino, R is hydrogen; or wherein $R_5$, Q, and the nitrogen atom taken together form a 5 or 6 membered ring; and wherein R is hydrogen or a carboxylic acid protecting ester forming group; and when R is hydrogen, the pharmaceutically acceptable non-toxic salts of the acids represented thereby; and wherein $R_1$ is hydrogen or an acyl group of the formula

wherein R' is (a) $C_1$-$C_7$ alkyl, $C_3$-$C_7$ alkenyl, cyanomethyl, halomethyl, 4-protected amino-4-protected carboxybutyl; or b. the group -R" wherein R" is 1,4-cyclohexadienyl, phenyl, or substituted phenyl wherein the substituents are halogen, hydroxy, nitro, cyano, trifluoromethyl, $C_1$-$C_4$ alkyl, $C_1$-$C_4$ alkoxy, hydroxymethyl, or protected aminomethyl; or c. an arylalkyl group of the formula R"—(Y)m—CH$_2$— wherein R" is as defined above,
Y is O or S, and
m is 0 or 1; or d. a substituted arylalkyl group of the formula

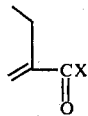

wherein R''' is R" as defined above, 2-thienyl, or 3-thienyl; W is hydroxy or protected hydroxy, carboxy or protected carboxy, amino, protected amino; or e. a heteroarylmethyl group of the formula

R''''CH$_2$— wherein R'''' is 2-thienyl, 3-thienyl, 2-furyl, 3-furyl, 2-thiazolyl, 5-tetrazolyl or 1-tetrazolyl; and wherein $R_2$ is hydrogen or methoxy; and
$q$ is 1 or 0 with the limitation that when $q$ is 1,
Z is

and $R_2$ is hydrogen.

The terms employed in the foregoing definition of the compounds of the present invention have the following meanings when employed herein. The term "$C_1$-$C_6$ alkyl" refers to methyl, ethyl, n-propyl, n-butyl, isobutyl, pentyl, n-hexyl, cyclohexyl, and like aliphatic hydrocarbon chains. "$C_3$-$C_7$ alkenyl" has reference to the unsaturated hydrocarbon chains such as propenyl (allyl), butenyl, pentenyl, hexenyl, heptenyl, and the like. "Halomethyl" refers to chloromethyl, bromomethyl, or iodomethyl. The term "$C_2$-$C_5$ alkylcarbonyldioxy" refers to such groups as methylcarbonyldioxy, ethylcarbonyldioxy, n-propylcarbonyldioxy, isobutylcarbonyldioxy, isopropylcarbonyldioxy and like groups. The term "$C_2$-$C_6$ haloalkyl" as employed in the above definition has reference to 2-bromoethyl, 2-iodomethyl, 2-bromopropyl, 2-iodopropyl, 2-bromobutyl, 2-bromo-2-methylpropyl, 2-bromobutyl, 2-bromo-2-methylbutyl and like groups. "$C_2$-$C_5$ alkanoyloxymethyl" refers to acetoxymethyl, propionyloxymethyl or pivaloyloxymethyl.

Illustrative of the groups -$SR_4$ as defined above are methylthio, ethylthio, n-propylthio, isopropylthio, tert-butylthio, phenylthio, benzylthio, 1-methyl-1,2,3,4-tetrazol-5-ylthio, 1,3,4-thiadiazol-2-ylthio, and like groups.

Included within the above definition of the group —$OR_3$ are hydroxy, methoxy, ethoxy, n-propoxy, isopropoxy, 2-bromoethoxy, n-butoxy, 2-iodoethoxy, 2-bromobutoxy, 2-bromopropoxy, 2,2,2-trichloroethoxy, p-methoxybenzyloxy, benzyloxy, p-nitrobenzyloxy, phenoxy, diphenylmethoxy, acetoxymethoxy and like groups.

Representative of the groups of the formula

as defined above are amino, methylamino, ethylamino, dimethylamino, diethylamino, isopropylamino, butylamino, cyclohexylamino, benzylamino, methoxyamino, hydroxyamino, methylphenylamino, methylhydroxyamino, phenylamino, benzyloxyamino, phenylhydrazino, acetylhydrazino, isopropylhydrazino, guanidino, morpholino, piperidino, pyrrolidino and like groups.

When in the above definition R" represents a substituted phenyl group, R" can be a mono or disubstituted halophenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono or dihydroxyphenyl group such as 4-hydroxyphenyl, 3-hydroxyphenyl, 2,4-dihydroxyphenyl and the like; a mononitrophenyl group such as 3- or 4-nitrophenyl; a cyanophenyl group, for example, 4-cyanophenyl; a mono or disubstituted lower alkylphenyl group such as 4-methylphenyl, 2,4-dimethylphenyl, 2-methylphenyl, 4-isopropylphenyl, 4-ethylphenyl, 3-n-propylphenyl and the like; a mono or disubstituted lower alkylphenyl ether for example, 2,6-dimethoxyphenyl, 4-methoxyphenyl, 3-ethoxyphenyl, 4-isopropoxyphenyl, 4-t-butoxyphenyl, 3-ethoxy-4-methoxyphenyl and the like. Also, R" represents disubstituted phenyl groups wherein the substituents can be different for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and like disubstituted phenyl groups bearing different substituents.

The term, "protected amino" as employed in the above definition has reference to an amino group substituted with one of the commonly employed amino blocking groups such as the t-butoxycarbonyl group (t-BOC); the benzyloxycarbonyl group, the p-methoxybenzyloxycarbonyl group, the p-nitrobenzyloxycarbonyl group, the 2,2,2-trichloroethoxycarbonyl group, the 1-carbomethoxy-2-propenyl group formed with methyl acetoacetate, the trimethylsilyl group, and like amino protecting groups.

The term "protected hydroxy" has reference to the readily cleavable groups formed with an hydroxyl group such as the formyloxy group, the chloroacetoxy group, the benzhydryloxy group, the trityloxy group, the p-nitrobenzyloxy group, the trimethylsilyl group, and the like.

The term "protected carboxy" has reference to a carboxy group which has been protected by one of the commonly used carboxylic acid protecting ester groups employed to block or protect the carboxylic acid functionality while reactions involving other functional sites of the compound are carried out. Such protected carboxy groups are noted for their ease of cleavage by hydrolytic or by hydrogenolytic methods to the corresponding carboxylic acid. Examples of carboxylic acid protecting groups include tert-butyl, benzyl, p-methoxybenzyl, $C_2$-$C_6$ alkanoyloxymethyl, $\beta$-iodoethyl, p-nitrobenzyl, diphenylmethyl (benzhydryl), phenacyl, p-halophenacyl, 2,2,2-trichloroethyl and like ester forming moieties. The nature of such ester forming groups is not critical so long as the ester formed therewith is stable under the reaction conditions described hereinafter. Preferred carboxylic acid protecting groups are benzhydryl, p-nitrobenzyl, tert-butyl, $\beta,\beta,\beta$-trichloroethyl, p-methoxybenzyl, and $\beta$-iodoethyl; most preferred are benzhydryl, p-methoxybenzyl and tert-butyl.

In the foregoing definitions, hydroxy, amino, and carboxy protecting groups are not exhaustively defined. The function of such groups is to protect the reactive functional groups during the preparation of the desired products and then be removed without disrupting the remainder of the molecule. Many such protecting groups are well known in the art and the use of other groups equally applicable to the process and compounds of the present invention, such as those described in J. F. W. McOmie, "Protective Groups in Organic Chemistry", Plenum Press, 1973, will be recognized as suitable. Thus, there is no novelty or inventiveness asserted with regard to the "protecting groups" alluded to in this specification.

Illustrative of the acyl groups,

as defined above are acetyl, propionyl, butyryl, hexanoyl, heptanoyl, 2-pentenoyl, acryloyl, 5-aminoadipoyl, chloroacetyl, bromoacetyl and the like.

Representative of the acyl groups

are benzoyl, 2,6-dimethoxybenzoyl, 4-chlorobenzoyl, 4-methylbenzoyl, 3,4-dichlorobenzoyl, 4-cyanobenzoyl, 3-bromobenzoyl, 3-aminobenzoyl, 4-nitrobenzoyl and the like.

Illustrative of the acyl groups

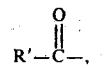

when R' is a group of the formula R''—(Y)m—CH$_2$— and m is 0, are cyclohexa-1,4-diene-1-acetyl, phenylacetyl, 4-chlorophenylacetyl, 3-hydroxyphenylacetyl, 3-cyanophenylacetyl, 4-hydroxy-3-methylphenylacetyl, 4-bromophenylacetyl, 4-ethoxyphenylacetyl, 4-nitrophenylacetyl, 3,4-dimethoxyphenylacetyl and the like; and when *m is* 1 'and Y is O, representative acyl groups are phenoxyacetyl, 3-hydroxyphenoxyacetyl, 4-chlorophenoxyacetyl, 3,4-dichlorophenoxyacetyl, 2-chlorophenoxyacetyl, 4-methoxyphenoxyacetyl, 2-ethoxyphenoxyacetyl, 3,4-dimethylphenoxyacetyl, 4-isopropylphenoxyacetyl, 3-cyanophenoxyacetyl, 3-nitrophenoxyacetyl and like substituted phenoxyacetyl groups; and when *m* is 1 and Y is S, representative phenylthioacetyl groups are phenylthioacetyl, 2,5-dichlorophenylthioacetyl, 3-chloro-4-fluorophenylthioacetyl, 4-cyanophenylthioacetyl, 3-bromophenylthioacetyl, and like acyl groups.

Illustrative of the acyl groups when R' is a substituted arylalkyl group of the formula

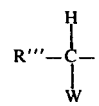

are the hydroxy substituted arylalkyl groups such as the 2-hydroxy-2-phenylacetyl group of the formula

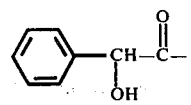

or the 2-formyloxy-2-phenylacetyl group of the formula

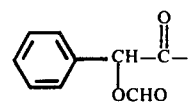

and similar groups wherein the phenyl ring is substituted, for example, 2-hydroxy-2-(4-methoxyphenyl)acetyl, 2-hydroxy-2-(3-chloro-4-hydroxyphenyl)acetyl, 2-formyloxy-2-(4-hydroxyphenyl)acetyl, 2-hydroxy-2-(3-bromophenyl)acetyl, 2-formyloxy-2-(3,5-dichloro-4-hydroxyphenyl)acetyl, 2-formyloxy-2-(3-chloro-4-methoxyphenyl)acetyl, 2-hydroxy-2-(3-chlorophenyl)acetyl and like groups.

Representative of the acyl groups when R' is a carboxy or alkoxycarbonyl substituted arylalkyl group are 2-phenyl-2-carboxyacetyl, 2-phenyl-2-tert-butoxycarbonylacetyl, 2-(4-chlorophenyl)-2-benzyloxycarbonylacetyl, 2-(4-methoxyphenyl)-2-carboxyacetyl, 2-(3-nitrophenyl)-2-carboxyacetyl, and like groups.

When R' is an amino substituted arylalkyl group or a derivative thereof, acyl groups represented thereby include 2-amino-2-phenylacetyl, 2-amino-2-(1,4-cyclohexadien-1-yl)acetyl, 2-phenyl-2-tert-butoxycarbonylamino)acetyl, 2-(4-hydroxyphenyl)-2-aminoacetyl, and the like acyl groups.

Representative of the acyl group

when R' is a heteroarylmethyl group of the formula R'''—CH$_2$— are 2-thienylacetyl, 3-thienylacetyl, 2-furylacetyl, a 2-thiazolylacetyl group of the formula

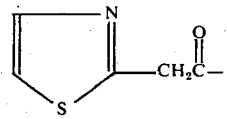

a 1-tetrazolylacetyl group of the formula

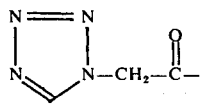

or a 5-tetrazolylacetyl group of the formula

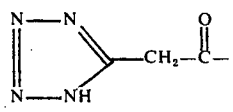

The compounds of the present invention of the formula

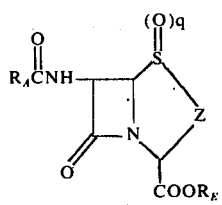

wherein Z is a group of the formula

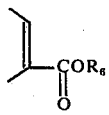

or

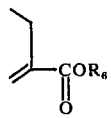

are prepared by a process which comprises reacting a compound of the formula

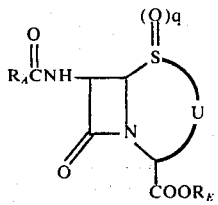

wherein U is a group of the formula

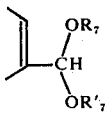

or

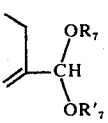

with 1–1.2 molar equivalents of N-bromosuccinimide in the presence of a free radical initiator in an inert organic solvent at a temperature between about 20° and 100° C.; wherein in the above formulae $R_E$ is a carboxylic acid protecting ester forming group; $R_4$ is a. $C_1$-$C_7$ alkyl, $C_3$-$C_7$ alkenyl, cyanomethyl, halomethyl, 4-protected amino-4-protected carboxybutyl; or b. the group R''– wherein R'' is 1,4-cyclohexyldienyl, phenyl, or substituted phenyl wherein the substituents are 1 to 3 halogens, hydroxy, nitro, cyano, trifluoromethyl, $C_1$-$C_4$ alkoxy, hydroxymethyl, or protected aminomethyl; or c. an arylalkyl group of the formula R''—(Y)m—CH$_2$— wherein R'' is as defined above,
Y is O or S, and
m is 0 or 1; or d. a heteroarylmethyl group of the formula

R''''CH$_2$— wherein R'''' is 2-thienyl, 3-thienyl, 2-furyl, 3-furyl, 2-thiazolyl, 5-tetrazolyl or 1-tetrazolyl;
and wherein $R_6$ is $C_1$-$C_6$ alkyl or $C_1$-$C_6$ 2-haloalkyl; $R_7$ and $R'_7$ are $C_1$-$C_6$ alkyl or $C_1$-$C_6$ 2-haloalkyl or $R_7$ and $R'_7$ taken together with the

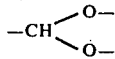

functionality form a dioxolane of the formula

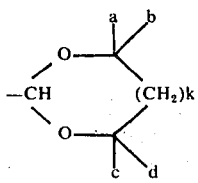

wherein *a*, *b*, *c*, and *d* are independently hydrogen methyl or ethyl such that *a*, *b*, *c*, and *d* together do not contain more than 6 carbon atoms; *k* is 1 or 0; and *q* is 1 or 0 with the limitation that when *q* is 1, Z is

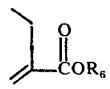

and U is

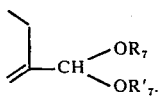

The compounds of the present invention other than the 3-alkoxycarbonyl or 3-(2-haloalkoxy)carbonyl compounds directly available via the NBS oxidation of the acetal intermediates, are derived from the 3-(2-haloalkoxy)carbonyl compounds through the 3-carboxylic acid intermediates. In general the preparation of the biologically active compounds of the present invention may be summarized as follows: (1) preparation of a 7-acylamino-3-formylcephem-4-carboxylic acid ester starting material (2) preparation of an acetal derivative (cyclic or acyclic) of the 3-formyl functionality; (3) conversion of the acetal to the corresponding cephem-3,4-dicarboxylic acid diester by reaction of the acetal with N-bromosuccinimide in the presence of a free radical initiator; (4) deesterification of the 3-carboxylic acid ester functionality to give the corresponding cephem-3-carboxylic acid 4-carboxylic acid ester; (5) preparation of first order derivative of the 3-carboxylic acid group by the reaction of a mixed anhydride or acid halide derivative of said 3-carboxylic acid group with an appropriate nucleophilic reagent; (6) isomerization to the corresponding 3-cephem derivative (if a 3-formyl-2-cephem was used as the starting material); and (7) removal of the 4-carboxylic acid ester protecting group. The 2-cephem to 3-cephem rearrangement (step 6 above) can alternatively be carried out on the products from step 3. In fact, depending on the nature of the desired final product, such a reaction sequence may be preferred. Furthermore, depending on the particularly desired product and the nature of the starting material, one or more of the reactions in the above designated sequence may not be necessary to prepare a biologically active compound of this invention. For example, the products from step 4, the 7-acylamino-3-carboxy-3-cephem-4-carboxylic acid esters, exhibit antimicrobial activity.

The 7-amino-3-(carboxy or substituted carboxy)-cephem-4-carboxylic acids and esters thereof are prepared from their respective 7-acylamino compounds by any one of a variety of side chain cleavage procedures known in the cephalosporin art, for example, those performed with nitrosyl chloride or with phosphorous pentachloride, pyridine and an alcohol. The 7-amino derivative thereby obtained can then be reacylated by known techniques to give preferred 7-acylamino side chains for maximum biological activity. Thus, the process for the preparation of the compounds of this invention can be carried out on starting materials having side chains most preferred for the preparative process (because of availability or stability to reaction conditions), and thereafter these side chains can be replaced by other 7-acylamino side chains preferred for maximum biological activity. For example, a 3-formyl cephem material derived from readily available cephalothin has the 2-thienylacetyl side chain which is stable under the reaction conditions employed in the preparation of the compounds of this invention. Although the cephem carboxylic acids of this invention having a 7-(2-thienylacetamido) substituent do exhibit antimicrobial activity, increased activity can be achieved by replacement of the 2-thienylacetyl group with, for example, an 2-formyloxy-2-phenylacetyl or 2-phenyl-2-carboxyacetyl group. Exemplary of the preparation of the compounds of the present invention starting with a 7-acylamino-3-formyl-2-cephem-4-carboxylic acid ester is the following reaction sequence:

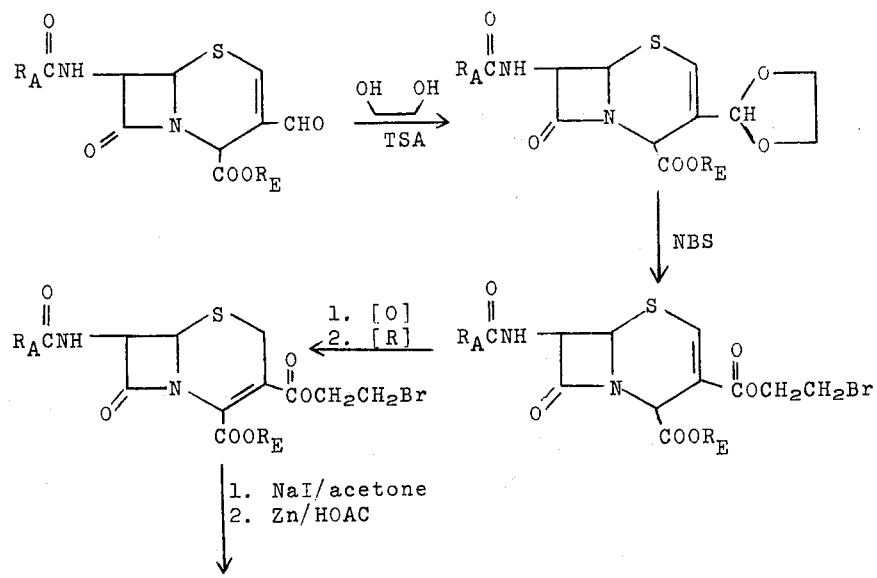

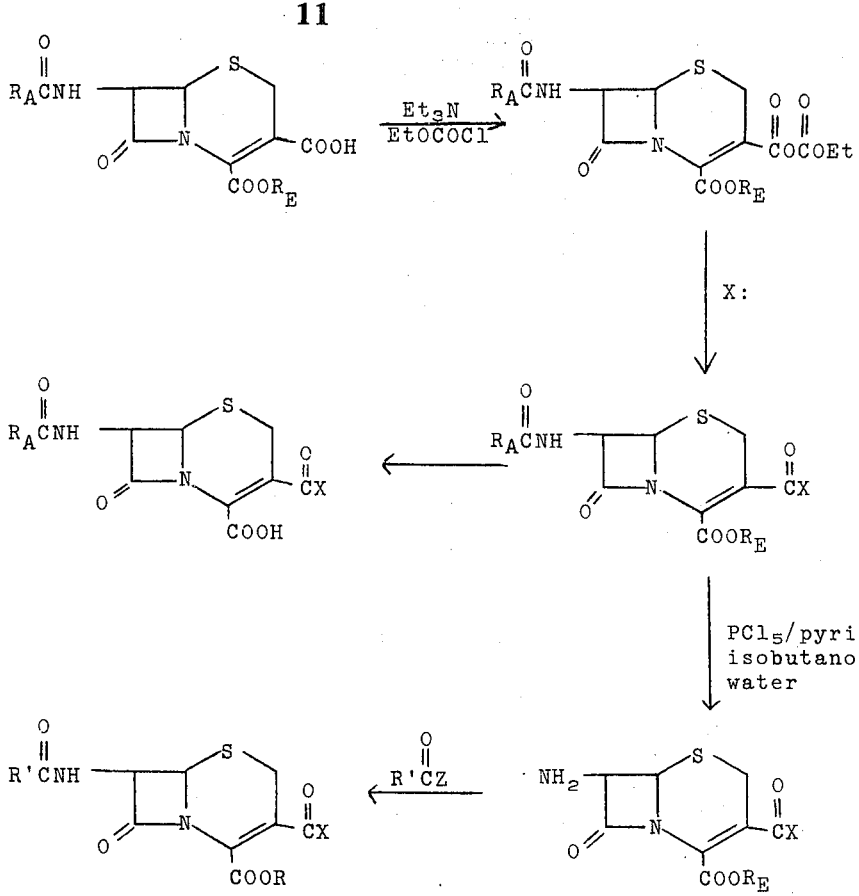

In the above formulae $R_A$, $R_E$, and $R'$ are as defined above.

The acetal intermediates employed in the preparation of the compounds of this invention are prepared by standard procedures from known 3-formyl cephalosporin derivatives. In addition to the 7-acylamino-3-formyl-2-cephem-4-carboxylic acid esters depicted in the above reaction sequence, both 7-acylamino-3-formyl-3-cephem-4-carboxylic acid esters of the formula

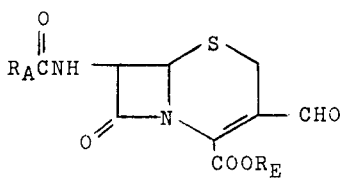

and 7-acylamino-3-formyl-3-cephem-4-carboxylic acid ester 1-oxide of the formula

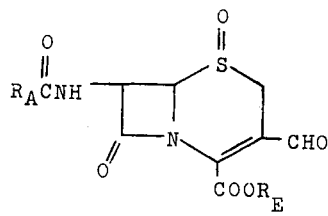

are suitable starting materials for said acetal intermediates.

In general the 3-formyl cephem compounds are prepared by oxidation of the corresponding 3-hydroxymethyl cephem derivatives with manganese dioxide or chromium trioxide. The use of chromium trioxide as the oxidizing agent, particularly chromium trioxide in sulfuric acid/water, commonly referred to as "Jones Reagent" [Fieser and Fieser, *Reagents in Organic Synthesis*, Vol. 1, page 142, John Wiley and Sons, Inc. 1967] is preferred.

The 7-acylamino-3-hydroxymethyl-3-cephem-4-carboxylic acids and esters, precursors to the 3-formyl compounds, are known in the cephalosporin art and are generally derived by known chemical or enzymatic procedures from 7-acylamino-3-acetoxymethyl-3-cephem-4-carboxylic acids and/or esters (derivatives of cephalosporin C). For example 7-phenoxyacetyl-3-acetoxymethyl-3-cephem-4-carboxylic acid can be treated with an esterase from *Bacillus subtilis* or with orange peel esterase to form 7-phenoxyacetyl-3-hydroxymethyl-3-cephem-4-carboxylic acid which can be esterified, e.g., with diphenyldiazomethane, to provide benzhydryl 7-phenoxyacetyl-3-hydroxymethyl-3-cephem-4-carboxylate. Oxidation of the resulting ester with chromium trioxide or manganese dioxide as described in U.S. Pat. No. 3,351,596 or with aliphatic sulfoxides in the presence of carboxylic acid anhydride as described in Belgium Patent 768653 results in the formation of a 3-formylcephem, a starting material for use in making the compounds of this invention. Alternatively, the 3-formylcephem compounds can be oxidized, e.g., with metachloroperbenzoic acid to the corresponding sulfoxide, also useful in the preparation of compounds of this invention. Such 3-formyl cephalosporin sulfoxide compounds and their preparation are described in particular in U.S. Pat. No. 3,674,784.

Several methods for the preparation of 3-formyl-2-cephem derivatives, a preferred class of starting materials for the compounds of the present invention, have been disclosed. These compounds were first described by Woodward et al. [*Journal of the American Chemical Society*, 88, 852 (1966)] as intermediates in the total synthesis of cephalosporin C. A process for the preparation of 7-acylamino-3-formyl-3-cephem-4-carboxylic acid esters has been described by Chamberlin et al. in the *Journal of Medicinal Chemistry*, 10, 967 (1967) wherein the corresponding 7-acylamino-3-hydroxymethyl-2-cephem-4-carboxylic acids are first esterified by known procedures, e.g., with diphenyldiazomethane. Subsequently, the resulting esters are oxidized to the 3-formyl derivatives with manganese dioxide or Jones Reagent as described hereinabove. For example, benzhydryl 7-thienylacetamido-3-formyl-2-cephem-4-carboxylate can be prepared from cephalothin, 7-(2-thienylacetamido)-3-acetoxymethyl-3-cephem-4-carboxylic acid, by (a) treatment with acetic anhydride and pyridine to provide the corresponding 2-cephem, (b) alkaline hydrolysis of the 3-acetoxymethyl-2-cephem (e.g., with dilute aqueous sodium hydroxide), to the corresponding 7-thienylacetamido-3-hydroxymethyl-2-cephem-4-carboxylic acid, (c) esterification with diphenyldiazomethane, and (d) oxidation of the resultant benzhydryl ester to the desired 3-formyl compound with Jones Reagent.

Alternatively, the 7-acylamino-3-hydroxymethyl-2-cephem-4-carboxylic acids can be oxidized directly to their 3-formyl derivatives using 2,3-dichloro-5,6-dicyano-1,4-benzoquinone as described in U.S. Pat. No. 3,682,903. Subsequent esterification of the product acids results in the preparation of a 7-acylamino-3-formyl-2-cephem-4-carboxylic acid ester starting material for the compounds of the present invention.

Illustrative of the 3-formylcephem derivatives useful as starting materials in preparing the compounds of the present invention are 4'-nitrobenzyl 7-acetamido-3-formyl-3-cephem-4-carboxylate,
benzhydryl 7-(2-thienylacetamido)-3-formyl-2-cephem-4-carboxylate,
$\beta,\beta,\beta$-trichloroethyl 7-phenoxyacetamido-3-formyl-2-cephem-4-carboxylate,
tert-butyl 7-chloroacetamido-3-formyl-3-cephem-4-carboxylate,
4'-methoxybenzyl 7-(2-furylacetamido)-3-formyl-2-cephem-4-carboxylate,
2'-iodoethyl 7-(4-bromobenzamido)-3-formyl-2-cephem-4-carboxylate,
benzhydryl 7-phenylacetamido-3-formyl-3-cephem-4-carboxylate 1-oxide,
4'-nitrobenzyl 7-(2-thienylacetamido)-3-formyl-3-cephem-4-carboxylate,
4'-methoxybenzyl 7-phenoxyacetamido-3-formyl-2-cephem-4-carboxylate,
benzhydryl 7-(4-chlorobenzamido)-3-formyl-3-cephem-4-carboxylate,
$\beta,\beta,\beta$-trichloroethyl 7-phenylthioacetamido-3-formyl-3-cephem-4-carboxylate,
benzhydryl 7-(3-thienylacetamido)-3-formyl-3-cephem-4-carboxylate 1-oxide,
benzhydryl 7-(4-tert-butoxycarbamido-4-tert-butoxycarbonylbutyl)-3-formyl-3-cephem-4-carboxylate,
4'-nitrobenzyl 7-(4-methoxybenzamido)-3-formyl-2-cephem-4-carboxylate,
2'-iodoethyl 7-(3-thienylacetamido)-3-formyl-2-cephem-4-carboxylate, and
4'-nitrobenzyl 7-phenoxyacetamido-3-formyl-3-cephem-4-carboxylate 1-oxide.

The process for preparing compounds of the present invention is applied to the acetal derivatives of 3-formylcephem compounds described hereinabove. The formation of acetals from carbonyl compounds and relatively low molecular weight alcohols has been well documented in the chemical literature. (See, e.g., R. B. Wagner and H. D. Zook, *Synthetic Organic Chemistry*, pp. 261–267, John Wiley and Sons, Inc. 1965).

Because of the availability of starting material and the relative ease of preparation, benzhydryl 7-(2-thienylacetamido)-3-formyl-2-cephem-4-carboxylate is a preferred precursor to the acetal intermediates of the process for preparing compounds of this invention.

When one of the above described 3-formyl cephem compounds, or a similar 3-formyl compound, is reacted with an alcohol or glycol in the presence of an acidic catalyst the corresponding acetal compound is formed. The reaction is preferably carried out in an inert organic solvent such as benzene or toluene which forms an azeotrope with water so that the water by-product of the acetalization can be conveniently removed by azeotropic distillation, thereby, favorably affecting the aldehyde-acetal equilibrium and forcing the reaction to completion. Alternatively, drying agents such as calcium chloride, calcium oxide, calcium carbide, or suitable molecular sieves can be employed to remove the water from the reaction mixture. In such cases, other organic solvents, inert to the reagents of the reaction, such as methylene chloride, chloroform, ethylene dichloride, dioxane, tetrahydrofuran, acetonitrile and like inert solvents, can also be employed.

Preferred acidic catalysts for acetal preparation include p-toluenesulfonic acid, hydrogen chloride and ferric chloride, sulfuric acid and phosphoric acid; p-toluenesulfonic acid is, however, the most preferred acidic catalyst for the preparation of the acetal intermediates to the compounds of this invention.

The nature of the acetals derived from the 7-acylamido-3-formylcephem-4-carboxylic acid esters and the percentage conversion to these derivatives depends upon the alcohol or glycol reactant. When alcohols such as methanol, ethanol, n-propanol, n-butanol, n-pentanol or n-hexanol are employed in acetal preparation, acyclic acetals are formed. Generally, higher yields of the acetals are achieved when lower molecular weight alcohols are employed in the acetalization. Furthermore, secondary alcohols such as isopropanol or sec-butanol may also be employed in preparation of the acyclic acetal derivatives, but the percentage conversion to the acetals is substantially reduced relative to that obtained with the corresponding primary alcohols. Preferred alcohols for the preparation of acyclic acetal intermediates useful in the preparation of the compounds of the present invention comprise methanol, ethanol, propanol, butanol, and like lower alkanols.

The 3-formylcephem compounds also condense with glycols, such as ethylene and propylene glycols, to form cyclic acetals, or dioxolanes. Suitable glycols which can be used for the preparation of the cyclic acetals include 1,2-ethanediol (ethylene glycol), 1,2-propanediol (propylene glycol), 2,3-butanediol, 2-methyl-1,3-propanediol, 1,2-butanediol, 2,3-pentanediol, 3,4-hexanediol, 2-methyl-1,2-propanediol and like lower dihydric alcohols. Ethylene glycol and propylene glycol are preferred glycol reagents for the preparation of the cyclic acetal intermediates. Ethylene glycol is most preferred.

The preferred method for acetalization of 7-acylamino-3-formylcephem compounds comprises reacting the 3-formyl derivative with a large excess of the alcohol or glycol in the presence of a catalytic amount of p-toluenesulfonic acid in refluxing benzene. Water is removed from the refluxing reaction mixture by the use of a Dean-Stark trap. After approximately 10 hours, or when water ceases to condense in the Dean-Stark trap, the reaction mixture is cooled and washed with a sodium bicarbonate solution. The acetal thereby obtained is conveniently purified by chromatography over silica gel.

Exemplary of the acetals which can serve as starting materials for the process of the present invention and which are available by the generally defined processes outlined hereinabove are the acyclic acetals:

benzhydryl 7-(2-thienylacetamido)-3-formyl-2-cephem-4-carboxylate dimethylacetal, 4'-nitrobenzyl 7-(3-nitrophenylacetamido)-3-formyl-3-cephem-4-carboxylate diethylacetal, $\beta,\beta,\beta$-trichloroethyl 7-(4-methoxyphenoxyacetamido)-3-formyl-3-cephem-4-carboxylate 1-oxide dimethylacetal, tert-butyl 7-(4-chlorophenoxyacetamido)-3-formyl-2-cephem-4-carboxylate di-n-butylacetal, 2'-iodoethyl 7-(2-furylacetamido)-3-formyl-3-cephem-4-carboxylate di-n-hexylacetal, benzhydryl 7-(4-chlorophenylthioacetamido)-3-formyl-2-cephem-4-carboxylate diisopropylacetal, 4'-methoxybenzyl 7-iodoacetamido-3-formyl-3-cephem-4-carboxylate 1-oxide diethylacetal;

and the cyclic acetals:

benzhydryl 7-(2-thienylacetamido)-3-(1,3-dioxolan-2-yl)-2-cephem-4-carboxylate, benzhydryl 7-(5-tetrazolylacetamido)-3-(4-methyl-1,3-dioxolan-2-yl)-2-cephem-4-carboxylate, 4'-nitrobenzyl 7-phenylacetamido-3-(1,3-dioxolan-2-yl)-3-cephem-4-carboxylate 1-oxide, $\beta,\beta,\beta$-trichloroethyl 7-phenoxyacetamido-3-(4,5-dimethyl-1,3-dioxolan-2-yl)-2-cephem-4-carboxylate, tert-butyl 7-acetamido-3-(4-ethyl-1,3-dioxolan-2-yl)-2-cephem-4-carboxylate, 4'-methoxybenzyl 7-chloroacetamido-3-(4-methyl-1,3-dioxolan-2-yl)-3-cephem-4-carboxylate 1-oxide, 2'-iodoethyl 7-benzamido-3-(1,3-dioxan-2-yl)-3-cephem-4-carboxylate, benzhydryl 7-(3-thienylacetamido)-3-(4,5-dimethyl-1,3-dioxolan-2-yl)-2-cephem-4-carboxylate, 4'-nitrobenzyl 7-(2-thiazolylacetamido)-3-(4-methyl-5-ethyl-1,3-dioxolan-2-yl)-2-cephem-4-carboxylate, benzhydryl 7-(1-tetrazolylacetamido)-3-(4,4-dimethyl-1,3-dioxolan-2-yl)-3-cephem-4-carboxylate, and tert-butyl 7-bromoacetamido-3-(4-methyl-1,3-dioxan-2-yl)-3-cephem-4-carboxylate.

Preferred 3-formylcephem acetal derivatives to be employed as starting materials for the preparation of the compounds of the present invention are the cyclic acetals derived from the 3-formyl compounds and ethylene or propylene glycol. Most preferred are those derived from ethylene glycol, namely those cephem esters having a 1,3-dioxolan-2-yl substituent at the 3-position. Illustrative of the most preferred acetal starting materials are benzhydryl 7-(2-thienylacetamido)-3-(1,3-dioxolan-2-yl)-2-cephem-4-carboxylate, benzhydryl 7-(2-thienylacetamido)-3-(1,3-dioxolan-2-yl)-3-cephem-4-carboxylate, tert-butyl 7-phenylacetamido-3-(1,3-dioxolan-2-yl)-2-cephem-4-carboxylate, 4'-methoxybenzyl 7-(2-thienylacetamido)-3-(1,3-dioxolan-2-yl)-2-cephem-4-carboxylate and like cephem derivatives having a 1,3-dioxolan-2-yl substituent at the C-3 position on the cephem ring.

The conversion of the above defined acetals to their corresponding 7-acylamino-3-carboxycephem-4-carboxylic acid diesters is accomplished by known oxidative procedures. Several cases of the conversion of acetals in general directly to esters have been reported in the chemical literature. Reagents which have been successfully employed in such conversions are ozone [P. Deslongchamps and C. Morean, *Canadian Journal of Chemistry*, 2463 (1971)] and N. bromosuccinimide [E. N. Marvell and J. J. Joncich, *Journal of the American Chemical Society*, 73, 973 (1951) and J. D. Prugh and W. C. McCarty, *Tetrahedron Letters*, 1351 (1966)]. A photochemical conversion of acetals to esters has also been reported [D. Elad and R. D. Youssefyeh, *Tetrahedron Letters*, 2189 (1963)].

Because of the presence of the double bond in the cephem ring system, neither the reaction with ozone nor the photochemical route to the 3-carboxy derivatives can be practically applied to the cephem acetal starting materials. The stability of the cephem ring system in the presence of N-bromosuccinimide (NBS), however, is well documented in the cephalosporin art; NBS has been successfully employed in the allylic bromination of the $C_3$-methyl of desacetoxycephalosporins. NBS is therefore the preferred reagent for the process of converting the above defined cephem acetal derivatives to the C-3 carboxylic acid esters of the present invention.

The acetal to ester conversion is exemplified for both cyclic and acyclic acetal derivatives in general by the following:

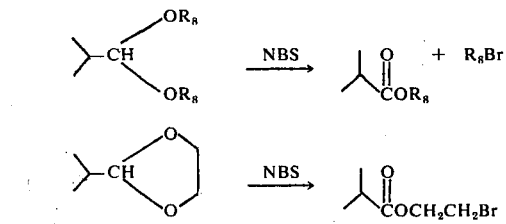

Oxidation of acyclic acetals with NBS provides esters derived from the alcohol employed in the acetal preparation. Thus, oxidation of dimethyl acetals results in methyl ester formation. Similarly diethyl acetals are oxidized to ethyl esters.

Cyclic ethylene acetals are oxidized with NBS to give $\beta$- (or 2-) bromoalkyl esters. In particular, ethylene acetals or substituted ethylene acetals, for example those derived from $\alpha,\beta$-alkanediols, e.g., 1,2-propanediol, are converted to the corresponding $\beta$-bromoalkyl ester, such as the $\beta$-bromoethyl ester or the $\beta$-bromopropyl ester. On the other hand, acetals derived from aldehydes and $\alpha,\gamma$-alkanediols, such as 1,3-propanediol, are converted to $\gamma$-bromoalkyl esters upon treatment with NBS.

In general, the acetal oxidation is carried out by reacting the acetal derivative with 1.0 to 1.2 molar equivalents of N-bromosuccinimide in the presence of a free radical initiator in an inert organic solvent at a temperature between about 10° and 100°C.

Suitable inert organic solvents are those which solubilize the starting material and are substantially inert under the conditions of the reaction, e.g. hydrocarbons such as benzene, toluene or chlorobenzene or halogenated hydrocarbons, particularly chlorinated hydrocarbons, e.g. chloroform, methylene chloride, 1,2-dichloromethane and like solvents. Benzene is a preferred solvent for the acetal oxidation step.

The reaction is preferably carried out in the presence of a suitable free radical initiator such as an azo compound, e.g. azobisisobutyronitrile, or a peroxide such as benzoyl peroxide. Radical initiation can also be effected by ultraviolet or visible light sources, e.g. mercury arcs or tungsten lamps, or by X-rays limited by $Co^{60}$ sources. Azobisisobutyronitrile is the most preferred radical initiator for the acetal oxidation step. It is employed only in trace amounts, as is characteristic of the use of such radical initiators. For example, 0.01 mmol of azobisisobutyronitrile is sufficient to effect the free radical oxidation of 26.8 mmol of benzhydryl 7-(2-thienylacetamido)-3-(1,3-dioxolan-2-yl)-2-cephem-4-carboxylate with 29.5 mmol of N-bromosuccinimide in refluxing benzene to benzhydryl 7-(2-thienylacetamido)-3-(2-bromoethoxycarbonyl)-2-cephem-4-carboxylate.

The oxidation can be effected at temperatures ranging from 20° to 100° C., preferably from 30° to 100° C. and most advantageously from about 40° to about 80° C.

The reaction is usually complete after about 15 minutes to about 2 hours, depending on the solvent, the particular acetal employed, and the temperature at which the reaction is performed. Generally, at the preferred reaction temperatures, the oxidation is complete within 15 to 30 minutes.

The preferred conditions and procedures employed in the preparation of 7-acylamino cephem-3,4-dicarboxylic acid diesters of the present invention are summarily delineated in the following description of the preparation of 4'-nitrobenzyl 7-(2-thienylacetamido)-3-(2-bromopropoxycarbonyl)-3-cephem-4-carboxylate from the corresponding 3-formyl cephem propylene cyclic acetal: A mixture of 5 mmol of 4'-nitrobenzyl 7-(2-thienylacetamido)-3-(4-methyl-1,3-dioxolan-2-yl)-3-cephem-4-carboxylate, 5.5 mmol of N-bromosuccinimide, and 0.05 mmol of azobisisobutyronitrile in 200 ml. of benzene is heated under reflux for 20 to 25 minutes and then cooled and evaporated to dryness. Chromatography of the resultant product mixture on silica gel using a toluene-ethyl acetate gradient provides 4'-nitrobenzyl 7-(2-thienylacetamido)-3-(2-bromopropoxycarbonyl)-3-cephem-4-carboxylate.

Illustrative of the 7-acylaminocephem-3,4-dicarboxylic acid diesters which are available by the above-described process are:

benzhydryl 7-(2-thiazolylacetamido)-3-(2-bromoethoxycarbonyl)-2-cephem-4-carboxylate,
4'-nitrobenzyl 7-phenoxyacetamido-3-methoxycarbonyl-3-cephem-4-carboxylate 1-oxide,
tert-butyl 7-acetamido-3-ethoxycarbonyl-3-cephem-4-carboxylate,
benzhydryl 7-phenylacetamido-3-(2-bromopropoxycarbonyl)-3-cephem-4-carboxylate,
4'-nitrobenzyl 7-(3-thienylacetamido)-3-(3-bromopropoxycarbonyl)-2-cephem-4-carboxylate,
4'-methoxybenzyl 7-(2-thienylacetamido)-3-(2-bromoethoxycarbonyl)-3-cephem-4-carboxylate,
$\beta,\beta,\beta$-trichloroethyl 7-(4-chlorophenoxyacetamido-3-(3-bromo-2-butoxycarbonyl)-2-cephem-4-carboxylate,
2'-iodoethyl 7-(3-furylacetamido)-3-methoxycarbonyl-3-cephem-4-carboxylate, and
tert-butyl 7-(2-thienylacetamido)-3-(2-bromoethoxycarbonyl)-2-cephem-4-carboxylate.

The 7-acylaminocephem-3,4-dicarboxylic acid diesters, compounds of the present invention, are useful intermediates for the preparation of the biologically active 3-cephem compounds of this invention which can be designated generally by the formula

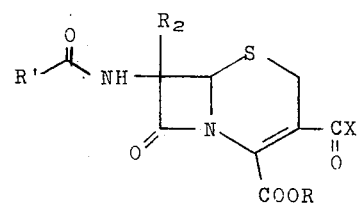

wherein X is (a) a group of the formula $-OR_3$, (b) a group of the formula $-SR_4$, or (c) a group of the formula

wherein R', $R_2$, $R_3$, $R_4$, $R_5$, and Q are as defined hereinabove; and R is hydrogen or, when $R_3$ is hydrogen or a pharmaceutically acceptable non-toxic cation, R is hydrogen or a carboxylic acid protecting group; and when R is hydrogen, the pharmaceutically acceptable non-toxic salts of the acids represented thereby.

The 3,4-dicarboxycephem diester intermediates can be converted directly to biologically active compounds of this invention by (a) transformation to a 3-cephem derivative (if diester is originally a 2-cephem), and (b) removal of the C-4 carboxylic acid ester protecting group, removal of the C-3 carboxy ester protecting group, or removal of both ester protecting groups.

The rearrangement of 2-cephem derivatives to the corresponding 3-cephem compounds is accomplished by an oxidation-reduction procedure well documented in the cephalosporin art. Generally, this procedure is carried out by first oxidizing the 2-cephem compound with, e.g., m-chloroperbenzoic acid, to give the corresponding 3-cephem 1-oxide derivative which is subsequently reduced via a trivalent phosphorous compound, such as phosphorous tribromide or phosphorous trichloride, preferably using dimethylformamide as a solvent.

It should be noted that this rearrangement step can be performed at any of several points in the process for preparing active compounds of the present invention. Preferably, the 2-cephem to 3-cephem conversion is carried out at a stage in the reaction sequence where the 2-cephem compound does not have a free carboxy or amino group. Thus, as applied to the preparation of the particular active compounds of the present invention, the conversion is generally performed on the 2-cephem intermediates of this invention having an acylamino group (with any carboxy or amino group, if present in the acyl moiety, protected) at C-7, an ester-protected carboxy group at C-4, and an ester, thioester or amide group at C-3. Although the point in the reaction sequence where the rearrangement is carried out is not critical, so long as the above described conditions are satisfied, experimentally it is most conveniently performed after the C-3 substituent desired in the final product has been obtained.

The 7-acylamino-3-cephem-3,4-dicarboxylic acid diesters, whether prepared directly from 3-cephem acetal derivatives or indirectly from 2-cephem acetal derivatives and subsequent isomerization to the 3-cephem, are converted to biologically active compounds of this invention by (a) deesterification of either or both of the carboxylic acid ester groups or by (b) deesterification of the C-4 ester group after deesterification of the C-3 ester functionality and conversion of the resultant 3-carboxylic acid group to a first order derivative thereof.

Cleavage of the ester moiety at C-4 to the free 4-carboxyl function is achieved by conventional methods, the specific method employed being dependent upon the particular ester protecting group present. For example, the benzhydryl, tert-butyl and p-methoxybenzyl groups are readily removed by treatment with an acid such as trifluoroacetic acid, usually in the presence of a carbonium ion stabilizer such as anisole. Deesterification of the $\beta,\beta,\beta$-trichloroethyl and 2-iodoethyl esters is accomplished by treatment with zinc and an acid such as formic acid, acetic acid or hydrochloric acid. Cleavage of the p-nitrobenzyl ester protecting group is usually accomplished by hydrogenating the ester in the presence of palladium, rhodium, or the like, in suspension or on a carrier such as barium sulfate, carbon, alumina, or the like. It should be noted that these techniques can likewise be employed to remove like protecting groups which may be present elsewhere in the cephem compounds.

Removal of the C-4 carboxylic acid ester protecting group of the 3-cephem diesters defined hereinabove results in the formation of 7-acylamino-3-alkoxycarbonyl (or haloalkoxycarbonyl)-3-cephem-4-carboxylic acids, preferred antibacterial compounds of the present invention. Illustrative of such compounds are 7-(2-thienylacetamido)-3-methoxycarbonyl-3-cephem-4-carboxylic acid,
7-phenylacetamido-3-(2-bromoethoxycarbonyl)-3-cephem-4-carboxylic acid,
7-phenoxyacetamido-3-(2-iodoethoxycarbonyl)-3-cephem-4-carboxylic acid,
7-(2,5-dichlorophenylthioacetamido-3-(2-bromopropoxycarbonyl)-3-cephem-4-carboxylic acid,
7-chloroacetamido-3-ethoxycarbonyl-3-cephem-4-carboxylic acid,
7-benzamido-3-bromoethoxycarbonyl-3-cephem-4-carboxylic acid,
7-(3-thienylacetamido)-3-(2-iodopropoxycarbonyl)-3-cephem-4-carboxylic acid, and
7-(2-thiazolylacetamido)-3-ethoxycarbonyl-3-cephem-4-carboxylic acid.

The 3-$\beta$-bromoalkyl ester group, derived from the corresponding cyclic ethylene acetal by the NBS-oxidation described hereinabove, can be cleaved directly with zinc and acetic acid to give the corresponding 3-carboxycephem compound. Preferably, however, the $\beta$-bromoalkyl ester group is first converted to the corresponding $\beta$-iodoalkyl ester which is subsequently cleaved to the carboxylic acid by treatment with 5 to 15 equivalents zinc and excess acetic acid at 0°–5° C. The application of this two-step process for the removal of a $\beta$-bromoalkyl ester group in cephalosporin compounds in particular has been described in Netherlands Patent No. 7,010,475. The $\beta$-iodoalkyl esters are derived from the $\beta$-bromoalkyl esters by reaction with 1.0–1.1 equivalents of sodium iodide in acetone at 30°–40° C. for 15-20 hours. This known conversion is accomplished in high yields with primary $\beta$-bromoalkyl ester groups, e.g. $\beta$-bromoethyl ester; yields with secondary $\beta$-bromoalkyl ester groups, e.g. $\beta$-bromo-n-propyl ester, are generally lower.

The deesterification of a 3-(2-bromoethoxycarbonyl) group of a hereinabove described 3,4-dicarboxycephem diester is, thus, preferably accomplished by a two-step process comprising (1) conversion to the corresponding iodoethyl ester by reacting the diester with 1 to 5 equivalents of sodium iodide in acetone at 35° for 16 hours; and (2) reductive removal of the resultant iodoethyl group, e.g. by reaction with about 10 equivalents of zinc dust in a 1:6 mixture of acetic acid and dimethylformamide at 0° for approximately 1.5 hours. Characteristic of many of the 3-carboxycephem-4-carboxylic acid esters thereby prepared is the solubility of the corresponding sodium salt in organic solvents; the acids are not extracted from ethyl acetate by a sodium bicarbonate solution. This property is utilized advantageously in the preparation of esters, thioesters, amides and other derivatives of the 3-carboxy group as described hereinbelow.

Exemplary of the active compounds of the present invention, available by deesterification of the 3-carboxylic acid ester group of 7-acylamino-3,4-dicarboxycephem diesters described hereinabove are:

benzhydryl 7-(1-tetrazolylacetamido)-3-carboxy-3-cephem-4-carboxylate,
tert-butyl 7-chloroacetamido-3-carboxy-3-cephem-4-carboxylate,
4'-methoxybenzyl 7-(4-cyanophenylacetamido)-3-carboxy-3-cephem-4-carboxylate,
tert-butyl 7-phenoxyacetamido-3-carboxy-3-cephem-4-carboxylate,
benzhydryl 7-(4-chlorobenzamido)-3-carboxy-3-cephem-4-carboxylate,
benzhydryl 7-acetamido-3-carboxy-3-cephem-4-carboxylate,
4'-methoxybenzyl 7-phenylthioacetamido-3-carboxy-3-cephem-4-carboxylic acid,
benzhydryl 7-(4-methoxyphenylacetamido)-3-carboxy-3-cephem-4-carboxylate,
4'-methoxybenzyl 7-(2-thienylacetamido)-3-carboxy-3-cephem-4-carboxylate,
tert-butyl 7-(3-thienylacetamido)-3-carboxy-3-cephem-4-carboxylate, and
benzhydryl 7-(2-furylacetamido)-3-carboxy-3-cephem-4-carboxylate.

7-Acylamido-3-cephem-3,4-dicarboxylic acids of the formula

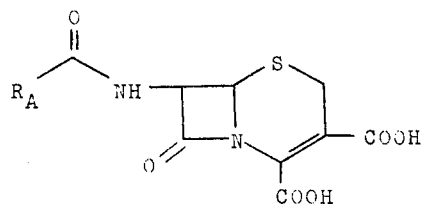

also active antimicrobial agents of the present invention, can be prepared directly from the cephem diesters having both ester groups susceptible to deesterification upon treatment with zinc and acetic acid. Thus, when $\beta$, $\beta,\beta$-trichloroethyl 7-(2-thienylacetamido)-3-(2-bromoethoxycarbonyl)-3-cephem-4-carboxylate is reacted with about 10 to 20 equivalents of zinc dust in glacial acetic acid or in a mixture of glacial acetic acid and a cosolvent, e.g. dimethylformamide, 7-(2-thienylacetamido)-3-cephem-3,4-dicarboxylic acid is prepared. likewise cephem diesters having a $\beta$-iodoethyl or p-nitrobenzyl ester at C-4 and a $\beta$-bromo(or iodo) alkyl ester group at C-3, under similar reaction conditions are converted to the corresponding cephem diacids. Similarly substituted 2-cephem diesters can be deesterified, providing directly, the corresponding 2-cephem-3,4-dicarboxylic acids.

Alternatively the cephem-3,4-dicarboxylic acids of this invention can be prepared from 7-acylamino-3-carboxy-3-cephem-4-carboxylic acid esters by employing the hereinabove described procedures for removal of the C-4 carboxylic acid esters protecting groups. For example, benzhydryl 7-(2-thienylacetamido)-3-carboxy-3-cephem-4-carboxylate is converted to 7-(2-thienylacetamido)-3-cephem-3,4-dicarboxylic acid by treatment with trifluoroacetic acid in the presence of anisole at 0°C. Illustrative of the 3-cephem diacids of the present invention available from 3-cephem diesters, either directly or via a 3-cephem-3,4-dicarboxylic acid ester intermediate, are 7-phenylacetamido-3-cephem-3,4-dicarboxylic acid,
7-phenoxyacetamido-3-cephem-3,4-dicarboxylic acid,
7-acetamido-3-cephem-3,4-dicarboxylic acid,
7-(5-tetrazolylacetamido)-3-cephem-3,4-dicarboxylic acid,
7-phenylthioacetamido-3-cephem-3,4-dicarboxylic acid,
7-chloroacetamido-3-cephem-3,4-dicarboxylic acid,
7-(3-nitrobenzamido)-3-cephem-3,4-dicarboxylic acid,
7-(4-methoxyphenylthioacetamido)-3-cephem-3,4-dicarboxylic acid,
7-(4-chlorophenylacetamido)-3-cephem-3,4-dicarboxylic acid,
7-(3-thiazolylacetamido)-3-cephem-3,4-dicarboxylic acid,
7-(2,5-dichlorophenylthioacetamido)-3-cephem-3,4-dicarboxylic acid,
7-(1,4-cyclohexadienylacetamido)-3-cephem-3,4-dicarboxylic acid,
7-(4-cyanophenoxyacetamido)-3-cephem-3,4-dicarboxylic acid, and
7-propionamido-3-cephem-3,4-dicarboxylic acid.

The 7-acylamino-3-carboxy-3-cephem-4-carboxylic acid esters, although themselves active compounds, are, along with the corresponding 2-cephem compounds, also preferred intermediates for the preparation of other active compounds of the present invention.

For example, these intermediates may be esterified with diazo compounds such as diphenyldiazomethane or p-nitrophenyldiazomethane to give the benzhydryl or p-nitrobenzyl esters at C-3 which are not available by techniques discussed hereinbefore. These intermediate compounds may also be used to prepare esters of the C-3 carboxy functionality, which although available by other preparative techniques (such as the above described NBS oxidation of acyclic acetals), are, because of higher overall yields, preferably prepared through the multi-step process, viz. via the 3-carboxycephem. For example, although cephem derivatives having a 3-methoxycarbonyl group are available by NBS oxidation of the corresponding 3-formylcephem dimethylacetal, compounds of this invention having this substituent are preferably prepared via esterification of a 7-acylamino-3-carboxy-3-(or 2)-cephem-4-carboxylic acid ester compound with, for example, diazomethane. Similarly other cephems having an alkyl ester substituent at $C_3$ can be prepared from the 3-carboxy cephem-4-carboxylic acid intermediates by a procedure described by Shaw et al. [*Tetrahedron Letters*, pp. 689–692 (1973)] whereby the sodium salt of the carboxylic acid is reacted with the desired alkyl iodide in hexamethylphosphoramide (HMPA) at room temperature. The preparation of the sodium salts of the 7-acylamino-3-carboxy-3(or 2)- cephem-4-carboxylic acid esters is described below. These salts react with alkyl iodides such as, methyl iodide, ethyl iodide, isopropyl iodide, and n-butyl iodide in HMPA at room temperature to give, after 24–48 hours, the corresponding esters in high yield. Likewise, the sodium salts of the 7-acylamino-3-carboxylic acid esters react with acyloxyalkyl halides in inert organic solvents, e.g. ethyl acetate, acetone, and dimethyl formamide, to provide the corresponding acyloxymethyl esters such as acetoxymethyl ester or pivaloyloxymethyl ester. Other C-3 carboxylic acid esters, e.g. trichloroethyl ester, p-methoxybenzyl ester or benzyl ester, can be prepared using conventional esterifying techniques and procedures well documented in the cephalosporin art as well as in other areas of general organic chemistry. Employing the hereinabove described procedures for rearrangement of a 2-cephem to a 3-cephem (if necessary) and for removal of the C-4 carboxylic acid ester protecting group provides the corresponding 7-acylamino-3-alkoxycarbonyl-3-cephem-4-carboxylic acids, preferred active compounds of the present invention.

The 7-acylamino-3-carboxy-3(or 2)-cephem-4-carboxylic acid esters can also be converted to their corresponding mixed anhydride or acid chloride derivatives which are useful in preparing other compounds of the present invention. Cephems having a first order derivative comprising amides, thioesters, esters (other than those available by the above described procedures), and acyl azides, of the C-3 carboxy group, are prepared by the reaction of the appropriate nucleophilic reagent with a mixed anhydride or acid halide derivative of a 7-acylamido-3-carboxy-3(or 2)-cephem-4-carboxylic acid ester. Such procedures for the preparation of carboxylic acid derivatives are well known in the cephalosporin art and common to other areas of organic chemistry. Esters, thioesters, and amides are thus routinely prepared by the reaction of the appropriate alcohol, thiol, or amine respectively with an activated carboxy functionality, e.g. an acid halide or mixed anhydride derivative.

The acid halide or mixed anhydride derivatives, also compounds of the present invention, are prepared from the 7-acylamino-3-carboxy-3(or 2)-cephem-4-carboxylic acid esters by known procedures. Generally the mixed anhydride derivatives of the present invention are prepared by a two-step procedure comprising (a) treatment of the 3-carboxy cephem compounds with 1 equivalent of a tertiary amine, such as triethylamine, N-methylmorpholine or diethylaniline, in an inert organic solvent at about −10° to 0° C. and (b) reacting the resultant tertiary amine salt with a $C_1$-$C_5$ alkyl chloroformate such as methyl chloroformate, ethyl chloroformate, propyl chloroformate, iso-butyl chloroformate or a like lower alkyl chloroformate. Exemplary of the mixed anhydrides available by this procedure are:

benzhydryl 7-(2-thienylacetamido)-3-ethylcarbonyldioxycarbonyl-3-cephem-4-carboxylate,
4'-methoxybenzyl 7-(3-thienylacetamido)-3-methylcarbonyldioxycarbonyl-3-cephem-4-carboxylate,
tert-butyl 7-phenylacetamido-3-isobutylcarbonyldioxycarbonyl-3-cephem-4-carboxylate,
benzhydryl 7-phenoxyacetamido-3-ethylcarbonyldioxycarbonyl-3-cephem-4-carboxylate,
4'-methoxybenzyl 7-acetamido-3-methylcarbonyldioxycarbonyl-3-cephem-4-carboxylate,
benzhydryl 7-(2-thiazolylacetamido)-3-n-butylcarbonyldioxycarbonyl-3-cephem-4-carboxylate,
tert-butyl 7-(2,5-dichlorophenylthioacetamido)-3-ethylcarbonyldioxycarbonyl-3-cephem-4-carboxylate, and the corresponding 2-cephem compounds.

These compounds can be isolated or reacted in situ with the desired nucleophilic reagents.

Acid halide derivatives of the 7-acylamino-3-carboxy-3(or 2)-cephem-4-carboxylic acid esters are prepared by the reaction of an appropriate halogenating agent and the sodium salt of the cephem acid. The sodium salts of the C-3-carboxylic acids are simply prepared by slurrying a solution of the acid in ethyl acetate with an aqueous sodium bicarbonate solution. The sodium salt, being soluble in ethyl acetate, remains in the organic layer, which can be separated and dried by conventional drying agents such as anhydrous sodium sulfate, anhydrous magnesium sulfate or molecular sieves. The sodium salt can, thus, be isolated or can be reacted in the ethyl acetate solution with the desired halogenating reagent to give the acid halide derivative. Preferably, the sodium salt is isolated and dried thoroughly before it is employed in the acid halide preparation. Generally the acid chloride derivatives are prepared by reaction of the 7-acylamino-3-carboxylic acid-3(or 2)-cephem-4-carboxylic acid ester sodium salt with 2-3 equivalents of oxalyl chloride in methylene chloride in the presence of several drops of dimethylformamide at 0° to −5° C. The acid chloride derivative is then isolated by evaporation of the reaction mixture at low temperature to dryness; it is used without purification to prepare the hereinabove described first order derivatives of the 7-acylamino-3-carboxy-3(or 2)-cephem-4-carboxylic acid esters. Acid bromide derivatives are prepared by a similar method using phosphorous tribromide or thionyl bromide as the halogenating agent. Illustrative of the acid halides of this invention which can be prepared by the above described procedures are:

benzhydryl 7-(2-thienylacetamido)-3-chlorocarbonyl-3-cephem-4-carboxylate,
benzhydryl 7-(4-tert-butoxycarbonyl-4-tert-butoxycarbamylbutyl)-3-chlorocarbonyl-3-cephem-4-carboxylate,
tert-butyl 7-(4-methoxyphenylacetamido)-3-chlorocarbonyl-3-cephem-4-carboxylate,
4'-methoxybenzyl 7-iodoacetamido-3-chlorocarbonyl-3-cephem-4-carboxylate,
benzhydryl 7-(4-chlorophenylthioacetamido)-3-chlorocarbonyl-3-cephem-4-carboxylate,
tert-butyl 7-acetamido-3-chlorocarbonyl-3-cephem-4-carboxylate,
benzhydryl 7-(3-thienylacetamido)-3-chlorocarbonyl-3-cephem-4-carboxylate,
4'-methoxybenzyl 7-benzamido-3-chlorocarbonyl-3-cephem-4-carboxylate,
the corresponding 2-cephem compounds, and the corresponding 2-cephem and 3-cephem-3-bromocarbonyl compounds.

Hereinbelow, for the purpose of simplicity, the acid halide (chloride and bromide) and the mixed anhydride derivatives of the 7-acylamino-3-carboxy-3(or 2)-cephem-4-carboxylic acid esters will at times be summarily denoted as "activated 3-carboxycephem" or as "activated 3-carboxycephem intermediates".

As mentioned hereinabove the acid halide and mixed anhydride derivatives of the 7-acylamino-3-carboxy-3(or 2)-cephem-4-carboxylic acid esters are preferred intermediates for the preparation of other cephem compounds of this invention having a first order derivative of the carboxy group at the C-3 position on the cephem ring. Thus, the activated 3-carboxycephem intermediates are reacted with alcohols to give cephem-3,4-dicarboxylic acid diesters, with thiols to provide cephems having a thioester group at C-3, or with amines or amine derivatives to provide cephems having an aminocarbonyl (carbamyl) group or derivative thereof at C-3. Likewise the reaction of activated 3-carboxycephem with azide ion (e.g. from sodium azide) gives the corresponding acyl azide.

Although several procedures for the preparation of 7-acylamino-3(or 2)-cephem-3,4-dicarboxylic acid diesters have been discussed hereinbefore, the activated 3-carboxycephem intermediates can likewise be employed in the diester preparation. The cephem diesters of this invention can be prepared by reacting alcohols with the activated 3-carboxycephem intermediates (acid halides or mixed anhydrides) in an inert organic solvent, e.g. methylene chloride, chloroform or tetrahydrofuran, usually in the presence of a basic reagent such as a tertiary amine or sodium bicarbonate. For example, benzhydryl 7-phenylacetamido-3-chlorocarbonyl-2-cephem-4-carboxylate is reacted with 4-methoxybenzyl alcohol in tetrahydrofuran in the presence of excess sodium bicarbonate to give benzhydryl 7-phenylacetamido-3-(4-methoxybenzoxycarbonyl)-2-cephem-4-carboxylate.

Cephems of this invention having a thioester function at C-3 can be prepared by reaction of the activated 3-carboxycephem intermediates of the present invention with mercaptans in an inert organic solvent, e.g. methylene chloride, chloroform, tetrahydrofuran, dioxane or acetonitrile. This is a standard procedure for the preparation of thioesters and is well documented in the chemical literature. Although the presence of a basic reagent, e.g. triethylamine or sodium carbonate is not essential to the preparation of these thioesters, such a reagent is preferably employed to lower the acidity of the reaction mixture, thus shortening the reaction time and increasing product yields.

Representative of the mercaptans which may be employed in preparing the thioesters of the present invention are methanethiol, ethanethiol, 2-propanethiol, 1-butanethiol, 2-methyl-2-butanethiol, 1-pentanethiol, 1-hexanethiol, thiophenol, benzylthiol, and heteroarylthiols such as 5-tetrazolethiol or 1,3,4-thiadiazol-2-thiol. For example, tert-butyl 7-(2,5-dichlorophenylthio)acetamido-3-ethylcarbonyldioxycarbonyl-3-cephem- 4-carboxylate is reacted with 1.1 equivalent 2-propanethiol in tetrahydrofuran in the presence of 1-10 equivalents of sodium bicarbonate at room temperature to provide tert-butyl 7-(2,5-dichlorophenylthio)acetamido-3-(2-propylthiol)carbonyl-3-cephem-4-carboxylate.

Specific illustrations of the thioester intermediates of the present invention which are available by the hereinabove described procedures are benzhydryl 7-phenoxyacetamido-3-(methylthio)carbonyl-3-cephem-4-carboxylate,
4'-methoxybenzyl 7-acetamido-3-[(1-pentylthio)carbonyl]-2-cephem-4-carboxylate,
tert-butyl 7-(1,4-cyclohexadienylacetamido)-3-[(2-propylthio)carbonyl]-3-cephem-4-carboxylate,
benzhydryl 7-(2-thienylacetamido)-3-(phenylthio)carbonyl-3-cephem-4-carboxylate,
benzhydryl 7-phenylacetamido-3-(benzylthio)carbonyl-2-cephem-4-carboxylate,
benzhydryl 7- [(4-chlorophenylthio)acetamido]-3-(1,2,3,4-tetrazol-5-mercapto)carbonyl-3-cephem-4-carboxylate,
4'-methoxybenzyl 7-(2-butenamido)-3-[(1,3,4-thiadiazol-2-mercapto)carbonyl]-3-cephem-4-carboxylate, and
tert-butyl 7-(2-thienylacetamido)-3-(ethylthio)carbonyl-2-cephem-4-carboxylate.

Biologically active cephem thioesters of the present invention are prepared from the above defined intermediates by converting to the 3-cephem derivatives (from 2-cephem compound) and removal of the C-4 carboxlic acid protecting group, procedures for which have been discussed hereinabove. Illustrative of the active thioesters of this invention available by the above described procedures are 7-(2-thienylacetamido)-3-(butylthio)carbonyl-3-cephem-4-carboxylic acid,
7-acetamido-3-(methylthio)carbonyl-3-cephem-4-carboxylic acid,
7-iodoacetamido-3-(phenylthio)acetamido-3-cephem-4-carboxylic acid,
7-phenylacetamido-3-(1,3,4-thiadiazol-2-mercaptocarbonyl)-3-cephem-4-carboxylic acid,
7-(1,4-cyclohexyldienylacetamido)-3-[(2-propylthio)-carbonyl]-3-cephem-4-carboxylic acid,
7-(2-thienylacetamido)-3-(hexylthio)carbonyl-3-cephem-4-carboxylic acid, and
7-(2-furylacetamido)-3-(ethylthio)carbonyl-3-cephem-4-carboxylic acid.

The activated 3-carboxycephem derivatives of this invention are converted to 3-aminocarbonyl or 3-substituted aminocarbonyl cephem compounds by reaction with 1 to 5 equivalents of a reagent bearing an amino group. Such a technique is the standard procedure for preparing amide derivatives and has been applied in many areas of organic chemistry, including those of penicillin and cephalosporin antibiotics, e.g. in the preparation of amide side chains of such compounds. Because of the susceptibility of the β-lactam functionality of the activated 3-carboxy cephem derivatives of this invention to attack by amines and amine derivatives, the preparation of the 3-amino (or substituted amino) carbonyl compounds of the present invention is preferably carried out at temperatures lower than those at which such amide forming reactions are usually performed; the problems associated with a possible competing β-lactam opening reaction are thus obviated or at least diminished. The reaction of amines or amine derivatives with the activated 3-carboxy cephem intermediates (acid chlorides or mixed anhydrides) is preferably carried out at −70° to −80°C. in an inert organic solvent, such as tetrahydrofuran, methylene chloride, chloroform, acetonitrile and like inert organic solvents.

The particular cephem derivative prepared depends, of course, on the nature of the amine or amine derivative employed in the preparative procedure.

The reaction of the above defined activated 3-carboxy cephem intermediates with ammonia gives the corresponding primary amide (a 3-aminocarbonylcephem). Such primary amide derivatives may also be prepared by reduction of the respective 3-azidocarbonyl cephem compounds described hereinafter.

Primary amines react with the 3-carboxycephem acid chloride or mixed anhydride derivatives under the above described conditions to give the corresponding secondary amides (3-monoalkyl or monoarylaminocarbonylcephems). Primary amine compounds which may be employed in preparing such compounds comprise methylamine, ethylamine, 2-propylamine, butylamine, cyclohexylamine, aniline, p-toluidine, benzylamine, and like primary amines. When secondary amines are employed in a similar procedure, the products formed are tertiary amines (3-disubstituted aminocarbonylcephems). Compounds included within the scope of the term "secondary amines" as used hereinabove for the process for preparing compounds of the present invention include dialkyl amines, such as dimethylamine, diethylamine, diisopropylamine, cyclohexylmethyl amine, benzylethylamine, and di-n-butylamine, arylalkylamines, such as N-methylaniline, N-ethylaniline, N-methyl-o-toluidine and N-isopropylaniline, cyclic amines, such as morpholine, piperidine, and pyrrolidine, and like amine compounds.

Benzhydryl 7-phenylacetamido-3-ethylcarbonyldioxycarbonyl-3-cephem-4-carboxylate reacts with 2 equivalents of tert-butylamine in tetrahydrofuran at −73° C. (dry ice - acetone bath) to provide benzhydryl 7-phenylacetamido-3-(tert-butylaminocarbonyl)-3-cephem-4-carboxylate. Likewise morpholine reacts under similar conditions with 4'-methoxybenzyl 7-(2-thienylacetamido)-3-bromocarbonyl-2-cephem-4-carboxylate to provide 4'-methoxybenzyl 7-(2-thienylacetamido)-3-morpholinocarbonyl-3-cephem-4-carboxylate. When tert-butyl 7-(1,4-cyclohexadienylacetamido)-3-(tert-butylcarbonyldioxycarbonyl)-3-cephem-4-carboxylate is reacted with 2.5 equivalents of N-methylaniline in methylene chloride at −76° C. for about 1 hour, the product isolated, after chromatography, is tert-butyl 7-(1,4-cyclohexadienylacetamido)-3-(N-methylanilinocarbonyl)-3-cephem-4-carboxylate.

Representative of the 3-aminocarbonyl compounds of the present invention available by the hereinabove described procedures are:

benzhydryl 7-[(2,5-dichlorophenylthio)acetamido]-3-aminocarbonyl-3-cephem-4-carboxylate,
benzhydryl 7-propionamido-3-methylaminocarbonyl-3-cephem-4-carboxylate,
tert-butyl 7-(4-methoxyphenylacetamido)-3-(diisopropylamino)carbonyl-2-cephem-4-carboxylate,
4'-methoxybenzyl 7-(3,4-dichlorobenzamido)-3-anilinocarbonyl-3-cephem-4-carboxylate,
tert-butyl 7-(1-tetrazolylacetamido)-3-piperidinocarbonyl-2-cephem-4-carboxylate, benzhydryl 7-(2-thienylacetamido)-3-pyrrolidinocarbonyl-3-cephem-4-carboxylate,
benzhydryl 7-phenylacetamido-3-(N-methyl-o-toluidinocarbonyl)-2-cephem-4-carboxylate,
tert-butyl 7-chloroacetamido-3-aminocarbonyl-3-cephem-4-carboxylate, and
4'-methoxybenzyl 7-[(2,5-dichlorophenylthio)acetamido]-3-ethylaminocarbonyl-3-cephem-4-carboxylate.

Compounds bearing an amino group (i.e. those having a nucleophilic nitrogen atom with an active hydrogen atom) other than the amino compounds mentioned heretofore react similarly with the activated 3-carboxycephem compounds of this invention to provide the expected first order derivatives of the 3-carboxycephams. Such amino compounds include hydroxylamine, $C_1$-$C_7$ alkoxyamines hydrazine, phenylhydrazine, $C_1$-$C_3$ hydrazides, and guanidine.

In general, the reactions of these compounds are carried out under the same conditions as delineated hereinabove for the reaction of the primary and secondary amine compounds with the activated 3-carboxycephem derivatives.

Hydroxylamines react with 7-acylamino 3-"activated" carboxy-3(or 2)-cephem-4-carboxylic acid esters at low temperature (−70° to −80° C.) to give the corresponding hydroxamic acid derivatives. Exemplary of such hydroxylamine reagents are hydroxylamine, methylhydroxylamine, ethylhydroxylamine, phenylhydroxylamine, propylhydroxylamine and o-tolylhydroxylamine. Alkoxyamines react with the activated 3-carboxy cephem derivatives to provide the respective hydroxamic acid esters. Representative of the alkoxyamines which may be employed in preparing hydroxamic acid esters of the present invention are methoxyamine, ethoxyamine or benzyloxyamine.

Hydroxylamine and its derivatives, exemplified by the above compounds, will in most cases, be used or added to the reaction mixture in the form of an acid salt of the amino group. Common acid salts used for this purpose are the hydrochloride or the p-tosylate (p-toluenesulfonate).

Benzhydryl 7-(2-thienylacetamido)-3-chlorocarbonyl-2-cephem-4-carboxylate reacts with 1.1 equivalents of methoxyamine in tetrahydrofuran at −76° C. to give benzhydryl 7-(2-thienylacetamido)-3-methoxyaminocarbonyl-2-cephem-4-carboxylate. 4'-Methoxybenzyl 7-butyramido-3-methylcarbonyldioxycarbonyl-3-cephem-4-carboxylate reacts with 1.1 equivalents phenylhydroxylamine in methylene chloride at −76° C. to provide 4'-methoxybenzyl 7-butyramido-3-phenylhydroxyaminocarbonyl-3-cephem-4-carboxylate.

Specific illustrations of the hydroxamic acids and esters thereof within the scope of the present invention are:
 benzhydryl 7-(4-fluorophenylacetamido)-3-hydroxyaminocarbonyl-3-cephem-4-carboxylate,
 4'-methoxybenzyl 7-(2-thienylacetamido)-3-methylhydroxyaminocarbonyl-2-cephem-4-carboxylate,
 tert-butyl 7-(4-methoxyphenylacetamido)-3-methoxyaminocarbonyl-3-cephem-4-carboxylate,
 benzhydryl 7-[(2,5-dichlorophenylthio)acetamido]-3-benzyloxyaminocarbonyl-2-cephem-4-carboxylate,
 benzhydryl 7-acetamido-3-ethylhydroxaminocarbonyl-3-cephem-4-carboxylate,
 tert-butyl 7-phenoxyacetamido-3-(o-tolylhydroxaminocarbonyl)-3-cephem-4-carboxylate,
 4'-methoxybenzyl 7-(4-cyanobenzamido)-3-ethoxyaminocarbonyl-2-cephem-4-carboxylate,
 4'-methoxybenzyl 7-(2-thienylacetamido)-3-phenylhydroxaminocarbonyl-2-cephem-4-carboxylate, and
 benzhydryl 7-(4-trifluoromethylphenylacetamido)-3-methoxyaminocarbonyl-3-cephem-4-carboxylate.

Other nucleophilic nitrogen containing compounds which can be employed in preparing amide-like derivatives of the C-3 carboxylic acid functionality include hydrazine, phenylhydrazine, hydrazides, such as acethydrazide or propionohydrazide, and guanidine. Such compounds react with the activated 3-carboxycephem intermediates of the present invention under the same conditions as defined hereinabove for primary and secondary amine compounds, i.e., in an inert inorganic solvent at low temperatures. For example, benzhydryl 7-acetamido-3-ethylcarbonyldioxycarbonyl-2-cephem-4-carboxylate reacts with 1.0 equivalent of phenylhydrazine in methylene chloride at −76° C. to provide benzhydryl 7-acetamido-3-phenylhydrazinocarbonyl-2-cephem-4-carboxylate. Similarly, tert-butyl 7-benzamido-3-chlorocarbonyl-3-cephem-4-carboxylate reacts with 1.0 equivalent of acethydrazide in tetrahydrofuran at −76° C. to give tert-butyl 7-benzamido-3-acetylhydrazinocarbonyl-3-cephem-4-carboxylate.

Exemplary of other cephem compounds of the present invention prepared by the reaction of activated 3-carboxycephem derivatives and guanidine, hydrazine, phenylhydrazine or hydrazides are benzhydryl 7-(2-thienylacetamido)-3-guanidinocarbonyl-2-cephem-4-carboxylate.
 tert-butyl 7-phenoxyacetamido-3-hydrazinocarbonyl-3-cephem-4-carboxylate,
 4'-methoxybenzyl 7-chloroacetamido-3-phenylhydrazinocarbonyl-3-cephem-4-carboxylate,
 tert-butyl 7-(2-thienylacetamido)-3-guanidinocarbonyl-2-cephem-4-carboxylate,
 benzhydryl 7-(2-furylacetamido)-3-hydrazinocarbonyl-3-cephem-4-carboxylate,
 benzhydryl 7-(2-chlorophenylaceamido)-3-acetylhydrazinocarbonyl-2-cephem-4-carboxylate, and
 4'-methoxybenzyl 7-propionamido-3-phenylhydrazinocarbonyl-3-cephem-4-carboxylate.

The activated 3-carboxycephem intermediates react also with other nucleophiles such as azide ion to provide the corresponding acyl azide. In general, the reaction with azide ion is performed similarly to the above described reactions of the mixed anhydride and acid halide compounds. A source of azide ion, e.g. sodium azide or tetramethylguanidinium azide, is reacted with the activated 3-carboxycephem intermediate in an inert organic solvent such as dioxane, tetrahydrofuran, or dimethylformamide at room temperature. The product 7-acylamino 3-azidocarbonyl-2(or 3)-cephem-4-carboxylic acid ester is a useful intermediate for the preparation of 7-acylamino-3-aminocarbonyl-3-cephem-4-carboxylic acids, active antimicrobial compounds of the present invention. The azidocarbonyl cephems are reduced by hydrogenation in methanol at 50 psi in the presence of 5 percent palladium on carbon catalyst (prereduced at 50 psi for 15 min.) to provide the corresponding amide derivative, a 7-acylamino-3-aminocarbonyl-3(or 2)-cephem-4-carboxylic acid ester.

Conversion of the hereinabove described cephem-4-carboxylic acid esters having a first order derivative of a carboxy group at C-3 to the active 3-cephem-4-carboxylic acids of this invention is accmplished by procedures previously described within this application. If the intermediate ester is a 2-cephem derivative, it is first rearranged to the corresponding 3-cephem compound by the hereinabove described oxidation-reduction procedure. The resultant 7-acylamino-3-(substituted)carboxy-3-cephem-4-carboxylate ester is then deesterified by employing such procedures as are appropriate for the removal of the particular ester protecting group. Thus, the tert-butyl, 4-methoxybenzyl and benzhydryl ester protecting groups are removed from the intermediate cephem-4-carboxylic acid esters by treatment with trifluoroacetic acid in anisole. Representative of the biologically active 7-acylamino-3-(substituted)aminocarboxy-3-cephem-4-carboxylic acids of the present invention are the following cephem acids:

7-acetamido-3-aminocarbonyl-3-cephem-4-carboxylic acid,
7-cyanomethyl-3-methylaminocarbonyl-3-cephem-4-carboxylic acid,
7-benzamido-3-isopropylaminocarbonyl-3-cephem-4-carboxylic acid,
7-(1,4-cyclohexadienylacetamido)-3-methoxyaminocarbonyl-3-cephem-4-carboxylic acid,
7-(phenylthio)acetamido-3-dimethylaminocarbonyl-3-cephem-4-carboxylic acid,
7-phenylacetamido-3-guanidinocarbonyl-3-cephem-4-carboxylic acid,
7-(2-thienylacetamido)-3-hydrazinocarbonyl-3-cephem-4-carboxylic acid,
7-(5-tetrazolylacetamido)-3-benzylaminocarbonyl-3-cephem-4-carboxylic acid,
7-phenoxyacetamido-3-benzyloxyaminocarbonyl-3-cephem-4-carboxylic acid,
7-(2-chlorophenylacetamido)-3-aminocarbonyl-3-cephem-4-carboxylic acid,
7-(4-nitrobenzamido)-3-acetylhydrazinocarbonyl-3-cephem-4-carboxylic acid,
7-(3-thienylacetamido)-3-anilinocarbonyl-3-cephem-4-carboxylic acid,
7-(4-chlorophenylacetamido)-3-diethylaminocarbonyl-3-cephem-4-carboxylic acid,
7-(2-thienylacetamido)-3-guanidinocarbonyl-3-cephem-4-carboxylic acid,
7-propionamido-3-cyclohexylaminocarbonyl-3-cephem-4-carboxylic acid,
7-phenylacetamido-3-hydroxaminocarbonyl-3-cephem-4-carboxylic acid,
7-(2-furylacetamido)-3-methoxyaminocarbonyl-3-cephem-4-carboxylic acid,
7-(2-thienylacetamido)-3-phenylhydrazinocarbonyl-3-cephem-4-carboxylic acid,
7-[(2,5-dichlorophenylthio)acetamido]-3-diisopropylaminocarbonyl-3-cephem-4-carboxylic acid,
7-phenylacetamido-3-piperidinocarbonyl-3-cephem-4-carboxylic acid, and
7-(1,4-cyclohexadienylacetamido)-3-cyclopropylaminocarbonyl-3-cephem-4-carboxylic acid.

As mentioned hereinbefore, the process for the preparation of the compounds of this invention can be carried out on starting materials having side chains most preferred for the preparative process (because of availability or stability to reaction conditions) and thereafter, such side chains can be replaced by other 7-acylamino side chains preferred for maximum biological activity. Intermediate in such a transacylation procedure is the corresponding 7-aminocephem derivative. The 7-amino-3-(substituted)carboxy-3-cephem-4-carboxylic acid esters, also compounds of this invention, are prepared by applying any one of a variety of known amide cleavage reactions to the respective 7-acylamino compounds. For example, the 7-acylamino-3-(substituted)carboxy-3-cephem-4-carboxylic acid ester can be cleaved by the well known $PCl_5$/pyridine:alcohol:water procedure as described, for example, in U.S. Pat. 3,697,515. Alternatively, a nitrosyl chloride cleavage procedure described in U.S. Pat. 3,261,832 can be used. Other 7-acyl cleavage procedures for cephalosporin compounds are described, e.g. in U.S. Pats. 3,272,809 and 3,507,860. A preferred procedure for cleaving the 7-acylamino side chain to provide the 7-amino derivatives comprises (a) reacting the 7-acylamino-3-(substituted) carboxy-3-cephem-4-carboxylic acid ester with about 1.0 to 1.2 equivalents of phosphorous pentachloride and pyridine at room temperature in an inert organic solvent, preferably methylene chloride, (b) reacting the iminochloride intermediate thereby formed with isobutanol at low temperature ($-10°$ C.) to provide the corresponding imino ether, and (c) hydrolyzing the imino ether with water. This cleavage procedure can be applied successfully to all 7-acylamino-3-(substituted)carboxy-3-cephem-4-carboxylic acid ester compounds of the present invention other than the 3-amino carbonyl or 3-substituted aminocarbonyl derivatives. For example, when benzhydryl 7-phenylacetamido-3-methoxycarbonyl-3-cephem-4-carboxylate is subjected to the above described reaction conditions, it is cleaved to the corresponding amino ester, benzhydryl 7-amino -3-methoxycarbonyl-3-cephem-4 -carboxylate. Exemplary of the nucleus esters of the present invention are:

benzhydryl 7-amino-3-(ethylthio)carbonyl-3-cephem-4-carboxylate,
4'-nitrobenzyl 7-amino-3-isopropoxycarbonyl-3-cephem-4-carboxylate,
4'-methoxybenzyl 7-amino-3-(4-nitrobenzyloxycarbonyl)-3-cephem-4-carboxylate,
tert-butyl 7-amino-3-(2-bromoethoxycarbonyl)-3-cephem-4-carboxylate,
$\beta,\beta,\beta$-trichloroethyl 7-amino-3-methoxycarbonyl-3-cephem-4-carboxylate,
benzhydryl 7-amino-3-(phenylthio)carbonyl-3-cephem-4-carboxylate,
benzhydryl 7-amino-3-benzhydryloxycarbonyl-3-cephem-4-carboxylate,
4'-nitrobenzyl 7-amino-3-(4-nitrobenzyloxycarbonyl)-3-cephem-4-carboxylate,
benzhydryl 7-amino-3-(4-nitrobenzyloxycarbonyl)-3-cephem-4-carboxylate,
tert-butyl 7-amino-3-cyclohexyloxycarabonyl-3-cephem-4-carboxylate,
4'-methoxybenzyl 7-amino-3-ethoxycarbonyl-3-cephem-4-carboxylate,
4'-nitrobenzyl 7-amino-3-(4-nitrobenzyloxycarbonyl)-3-cephem-4-carboxylate,
benzhydryl 7-amino-3-(2-iodoethoxycarbonyl)-3-cephem-4-carboxylate, and
4'-methoxybenzyl 7-amino-3-(2-bromopropoxycarbonyl)-3-cephem-4-carboxylate.

The nucleus acids, comprising 7-amino-3-(substituted) carbonyl-3-cephem-4-carboxylic acids, 7-amino-3-carboxy-3-cephem-4-carboxylic acid esters and the nucleus diacid, 7-amino-3-cephem-3,4-dicarboxylic acid, are preferably prepared from their respective 4-nitrobenzyl esters by hydrogenation in the presence of a palladium on carbon catalyst. For example, benzhydryl 7-amino-3-carboxy-3-cephem-4-carboxylate is prepared by hydrogenation of benzhydryl 7-amino-3-(4-nitrobenzyloxycarbonyl)-3-cephem-4-carboxylate. Similarly, the nucleus diacid can be prepared by hydrogenation of 4'-nitrobenzyl 7-amino-3-(4-nitrobenzyloxycarbonyl)-3-cephem-4-carboxylate. Representative of the nucleus acids, compounds of the present invention useful for preparing active antibiotics of this invention, are the following compounds:

benzhydryl 7-amino-3-carboxy-3-cephem-4-carboxylate,
4'-methoxybenzyl 7-amino-3-carboxy-3-cephem-4-carboxylate,
7-amino-3-methoxycarbonyl-3-cephem-4-carboxylic acid,
7-amino-3-cephem-3,4-dicarboxylic acid,
tert-butyl 7-amino-3-carboxy-3-cephem-4-carboxylate, 7-amino-3-(ethylthio)carbonyl-3-cephem-4-carboxylic acid,
7-amino-3-(2-bromopropoxycarbonyl)-3-cephem-4-carboxylic acid, and
β,β,β-trichloroethyl-7-amino-3-carboxy-3-cephem-4-carboxylate.

The nucleus acids and nucleus esters described hereinabove are useful intermediates for the preparation of those biologically active 7-acylamino-3-(substituted)-carbonyl-3-cephem-4-carboxylic acids of the present invention wherein the 7-acylamino group is not a particularly preferred group for the process of preparing the 3-carboxy function, but is preferred for antimicrobial activity.

Acylation of the nucleus acids or nucleus esters may be carried out by following known procedures used for the acylation of other cephalosporin nuclei, such as 7-ACA or 7-ADCA. For example, the nucleus ester can be reacted with an acyl halide, such as 0-formylmandeloyl chloride or 2-(tert-butoxycarbonyl)-2-phenylacetyl chloride, or a mixed anhydride derivative of the acid corresponding to the desired acyl group, such as that formed by the reaction of 2-(tert-butoxycarbonylamino)-2-phenylacetic acid N-methylmorpholine salt and methylchloroformate. Such an acylation is usually performed in an inert anhydrous organic solvent, e.g. methylene chloride, chloroform, dioxane, tetrahydrofuran, acetonitrile or ethyl acetate, in the presence of a hydrogen halide acceptor, for example, a tertiary amine, such as triethylamine, pyridine and N-methylmorpholine or an inorganic base such as sodium bicarbonate or sodium bisulfite. A preferred method of acylating the nucleus diesters of this invention comprises reacting the nucleus diester with an acid chloride derivative corresponding to the desired acyl group in the presence of sodium bicarbonate in tetrahydrofuran at 0° to 5° C. The product is isolated and purified by conventional chromatographic techniques. Alternatively, and in accordance with known methods, a nucleus diester can be acylated by its reaction with a carboxylic acid corresponding to the desired acyl group in the presence of a condensing agent such as dicyclohexylcarbodiimide or 2-ethoxy-N-ethoxycarbonyl-1,2-dihydroquinoline (EEDQ). For example, 2-phenyl-2-formyloxyacetic acid can be reacted with benzhydryl 7-amino-3-methoxycarbonyl-3-cephem-4-carboxylate under essentially anhydrous conditions to provide benzhydryl 7-(2-phenyl-2-formyloxyacetamido)-3-methoxycarbonyl-3-cephem-4-carboxylate. The nucleus diesters can also be acylated according to methods described in U.S. Pat. 3,502,664. The C-4 carboxylic acid ester protecting group of the acylated compounds thereby prepared is then removed by procedures described hereinabove. Either simultaneously, or subsequently, protecting groups of functionalities on the side chain, for example, the tert-butoxycarbonyl or 4-nitrobenzyloxycarbonyl employed in protecting an amino or hydroxy group, can be removed by procedures which are known to those skilled in the art.

Generally, the nucleus acid derivatives (7-amino-3-(substituted)carboxy-3-cephem-4-carboxylic acid, 7-amino-3-carboxy-3-cephem-4-carboxylic acid ester, or 7-amino-3-cephem-3,4-dicarboxylic acid) can be acylated by methods which have been employed in the acylation of 6-APA, 7-ACA and 7-ADCA. One such method involves the addition of an acid chloride to a suspension of the amino acid and urea in acaetone. Alternatively, the nucleus acid can be reacted with an acid anhydride derivative of the side chain acid in an inert anhydrous organic solvent such as acetone, ethyl acetate, methylene chloride or acetonitrile in the presence of a base, such as sodium bicarbonate, pyridine, triethylamine, N-methylmorpholine and the like. Furthermore, the amino acid derivative may be acylated to give the respective acylamino acid by first reacting the nucleus acid with a silylating agent, such as hexachlorodisilane, to form the corresponding silyl ester which is subsequently reacted with an active ester, for example, a pentachlorophenyl ester, of the acid corresponding to the desired side chain. A Schotten-Baumann type acylation may also be employed whereby the amino acid is reacted with the appropriate acid chloride in aqueous acetone in the presence of sodium bicarbonate.

Suitable acid chloride acylating agents which can be employed in preparing compounds of the present invention include phenylglycyl chloride hydrochloride, D-O-formylmandelic acid chloride, 2-phenyl-2-tert-butoxycarbonylacetyl chloride, D-2-(4-methoxyphenyl)-2-(4-nitrobenzyloxycarbonylamino)acetyl chloride, D-2-(4-hydroxyphenyl)-2-formyloxyacetyl chloride, (2,5-dichlorophenylthio)acetyl chloride, 2-(2-thienyl)-2-(tert-butoxycarbonylamino)acetyl chloride and like acid chlorides. Generally such compounds are prepared from their respective carboxylic acid salts via reaction with oxalyl chloride in an inert organic solvent in the presence of several drops of dimethylformamide.

Mixed anhydride reagents suitable for acylating the nucleus acids and nucleus diesters of the present invention include those which can be formed by the reaction of lower alkyl chloroformates, e.g. methyl chloroformate, ethyl chloroformate, or isobutyl chloroformate, and a sodium or tertiary amine salt of a carboxylic acid corresponding to the desired acyl substituent. Representative of carboxylic acids from which such mixed anhydride acylating agents may be prepared are mandelic acid, 2-phenyl-2-tert-butoxycarbonylacetic acid, 2-hydroxyphenyl-2-(4-nitrobenzyloxycarbonylamino)acetic acid, N-tert-butoxycarbonylphenylglycine, 2-(2-thienyl)-2-(2,2,2-trichloroethoxycarboxyamino)acetic acid, 2-(4-hydroxyphenyl)-2-formyloxyacetic acid, and like carboxylic acid compounds.

Illustrative of preferred substituted cephalosporin antibiotics of the present invention available by techniques discussed hereinbefore are
7-[D-(2-phenyl-2-formyloxyacetamido)]-3-(2-bromoethoxycarbonyl)-3-cephem-4-carboxylic acid,
7-[D-2-phenyl-2-(4-nitrobenzyloxycarbonylamino)acetamido]-3-methoxycarbonyl-3-cephem-4-carboxylic acid,
7-D-(2-phenyl-2-hydroxyacetamido)-3-cephem-3,4-dicarboxylic acid,
7-(2-phenyl-2-tert-butoxycarbonylacetamido)-3-thiomethoxycarbonyl-3-cephem-4-carboxylic acid,
7-(2-phenyl-2-carboxyacetamido)-3-carboxy-3-cephem-4-carboxylic acid,
7-(D-2-phenyl-2-aminoacetamido)-3-(phenylthio)-carbonyl-3-cephem-4-carboxylic acid,
7-(D-2-phenyl-2-formyloxyacetamido)-3-isopropoxycarbonyl-3-cephem-4-carboxylic acid,
7-(2-thienyl-2-aminoacetamido)-3-(4-nitrobenzyloxycarbonyl)-3-cephem-4-carboxylic acid,
7-[D-2-(4-methoxyphenyl)-2-formyloxyacetamido)]-3-benzyloxycarbonyl-3-cephem-4-carboxylic acid,
7-(D-2-phenyl-2-aminoacetamido)-3-cephem-3,4-dicarboxylic acid,
7-[D-2-(4-hydroxyphenyl)-2-hydroxyacetamido]-3-cephem-3,4-dicarboxylic acid,
7-[2-(2-thienyl)-2-tert-butoxycarbonylaminoacetamido]-3-benzhydryloxycarbonyl-3-cephem-4-carboxylic acid,
7-(D-2-phenyl-2-aminoacetamido)-3-(2-bromoethoxycarbonyl)-3-cephem-4-carboxylic acid,
7-(2-phenyl-2-carboxyacetamido)-3-(4-nitrobenzyloxycarbonyl)-3-cephem-4-carboxylic acid,
7-[4-chlorophenyl-2-(4-nitrobenzyloxycarbonylaminoacetamido]-3-(benzylthio)carbonyl-3-cephem-4-carboxylic acid, and
7-(2-phenyl-2-formyloxyacetamido)-3-(tert-butylthio) carbonyl-3-cephem-4-carboxylic acid.

Active cephalosporins of this invention having an aminocarbonyl (carbamyl) or a substituted aminocarbonyl group at C-3 and a side chain preferred for maximum antimicrobial activity at C-7 can be prepared from nucleus diesters of the formula

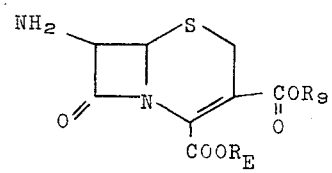

wherein $R_9$ is a removable ester protecting group, e.g. 2-bromoethyl, 4-nitrobenzyl, or benzhydryl and $R_E$ is as defined above with the limitation that the ester protecting groups may be removed independently. This conversion is accomplished by employing acylation and deesterification procedures discussed hereinabove. In general, the nucleus diester is first acylated with the desired acylating agent; the C-3 ester group is deesterified; the resulting C-3 carboxylic acid is converted to the (substituted)aminocarbonyl functionality via its acid chloride or mixed anhydride derivative; and in the final step, the C-4 ester group is deesterified and any side chain blocking groups are removed to provide an active cephalosporin compound of this invention. For example, benzhydryl 7-amino-3-(4-nitrobenzyloxycarbonyl)-3-cephem-4-carboxylate can be converted to 7-(2-phenyl-2-carboxyacetamido)-3-methylaminocarbonyl-3-cephem-4-carboxylic acid by performing the following reactions: (1) acylation with 2-phenyl-2-tert-butoxycarbonylacetyl chloride; (2) removal of the 4-nitrobenzyl group to provide benzhydryl 7-(2-phenyl-2-tert-butoxycarbonylacetamido)-3-carboxy-3-cephem-4-carboxylate; (3) preparation of the acid chloride or mixed anhydride of the C-3 carboxy group; (4) reaction of said acid chloride or mixed anhydride with methylamine at low temperature; and (5) removal of the benzhydryl and tert-butyl protecting groups. Preferred procedures for each of the above types of reactions have been discussed independently hereinbefore, and such procedures are applicable to the preparation of active 3-(substituted)aminocarbonyl cephems having a preferred side chain at C-7. Representative of such compounds are:

7[D-(2-phenyl-2-formyloxyacetamido)]-3-aminocarbonyl-3-cephem-4-carboxylic acid,
7-[D-(2-phenyl-2-hydroxyacetamido)]-3-dimethylaminocarbonyl-3-cephem-4-carboxylic acid,
7-(D-2-phenyl-2-aminoacetamido)-3-piperidinocarbonyl-3-cephem-4-carboxylic acid,
7-(D-2-thienyl-2-aminoacetamido)-3-methoxyaminocarbonyl-3-cephem-4-carboxylic acid,
7-(2-phenyl-2-carboxyacetamido)-3-hydroxyaminocarbonyl-3-cephem-4-carboxylic acid,
7-[(2,4-dichlorophenylthio)acetamido]-3-guanidinocarbonyl-3-cephem-4-carboxylic acid,
7-[D-2-(4-hydroxyphenyl)-2-hydroxyacetamido]-3-hydrazinocarbonyl-3-cephem-4-carboxylic acid,
7-[D-(4-methoxyphenyl)-2-formyloxyacetamido]-3-benzyloxycarbonyl-3-cephem-4-carboxylate,
7-[2-(2-thienyl)-2-aminoacetamido]-3-isopropylamino-3-cephem-4-carboxylic acid, and
7-(2-phenyl-2-carboxyacetamido)-3-acetylhydrazinocarbonyl-3-cephem-4-carboxylic acid.

The aforedescribed nucleus diesters are also useful for preparing 7-acylamino-7-methoxy-3-(substituted)-carbonyl-3-cephem-4-carboxylic acids, also active compounds of the present invention. In the first step for production of such 7-methoxy cephems of this invention, a nucleus diester of the formula

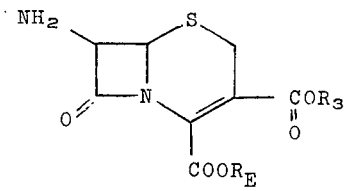

wherein $R_3$ and $R_E$ are as defined above with the limitation that $R_3$ is not hydrogen, is converted to its corresponding 7-(4-nitrobenzyloxycarbamido)cephem diester. This is accomplished by acylating the 7-amino compound with a haloformate ester of 4-nitrobenzyl alcohol. This acylation is carried out in an inert solvent in the presence of an acid scavenging reagent, for example, a tertiary amine such as triethylamine, N,N-diethylaniline, pyridine, or an inorganic base such as sodium or potassium bicarbonate or carbonate. Inert solvents which can be employed in the acylation reaction include, for example, acetone, ethyl acetate, acetonitrile, N,N-dimethylformamide, or any other suitable solubilizing agent. The haloformate esters of 4-nitrobenzyl alcohol which can be employed are the bromoformate and the chloroformate esters. Preferably, the chloroformate ester is employed.

The next step in producing the active compounds of this invention having a C-7 methoxy group involves reacting the 7-(4-nitrobenzyloxycarbamido)-3-cephem-3,4-dicarboxylic acid diester in an inert, anhydrous solvent at a temperature between about −120° C. and −25° C., and preferably between about −100° C. and −75° C., with from about 2 to about 6 molar equivalents of lithium methoxide in excess methanol to generate, in situ, the anionic form of the starting material represented by the formula

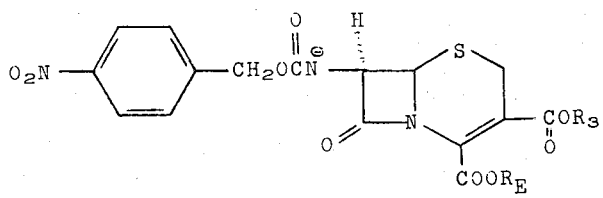

The above anionic form is generated rapidly and is substantially stable at the reaction temperature. The resulting reaction mixture is stirred for about 5 minutes to ensure completion of generaton of the anionic form. At least one molar equivalent of t-butyl hypochlorite is then added to the cold, stirred reaction mixture. Stirring is continued for an additional 15 to 20 minutes, and the mixture is then acidified, preferably with formic acid or a lower alkyl carboxylic acid such as glacial acetic acid. This provides a 7-methoxylated derivative of the formula

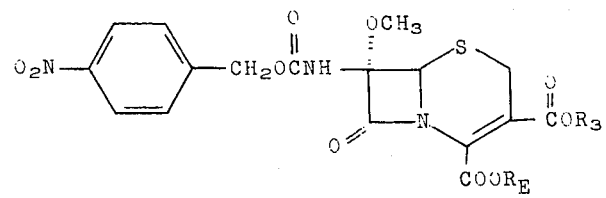

Upon completion of addition of the carboxylic acid, any excess t-butyl hypochlorite which may be present in the reaction mixture preferably is destroyed by adding trimethylphosphite to the cold acidified mixture in an amount corresponding to the excess of t-butyl hypochlorite used in the reaction.

Inert solvents which can be employed include, for example, tetrahydrofuran, dioxane, the dimethyl ether of ethylene glycol, N,N-dimethylformamide, and polyethers such as diethylene glycol dimethyl ether. Any suitable inert solvent which will provide a fluid reaction medium at the temperature of the reaction may be employed. However, such solvents should be substantially anhydrous since water may interfere with the anion formation and thereby reduce the yield of the methoxylated product. Preferably, tetrahydrofuran is employed as the solvent.

The aforedescribed methoxylation procedure, specific to a 7-(4-nitrobenzyloxycarbamido)cephem ester, employs procedures for the methoxylation of 7-acylamidocephalosporins described by G. A. Koppel and R. E. Koehler in the *Journal of the American Chemical Society*, 95, 2403 (1973).

The next step in preparing the 7-methoxy compounds of this invention involves cleavage of the 4-nitrobenzyloxycarbonyl group from the prepared 7-(4-nitrobenzyloxycarbamido)-7-methoxy-3-cephem-3,4-dicarboxylic acid diester. The 4-nitrobenzyloxycarbonyl group can be cleaved by a two-step procedure which includes, first, the mild reduction of the 7-(4-nitrobenzyloxycarbamido) group to obtain an intermediate reduction product, and, secondly, the treatment of the reduction product under mildly acidic conditions to effect removal of the reduced side chain.

When the first step of the two-step cleavage reaction involves reduction by hydrogenation, the substrate preferably is dissolved in an inert organic solvent and hydrogenated in the presence of a palladium catalyst until hydrogen absorption ceases. The hydrogenation is carried out generally between about 20° and 35° C., preferably at about room temperature, and under a hydrogen pressure of from about 1 to 5 atmospheres. Reduction proceeds slowly with hydrogen uptake continuing over a period of about 12 hours. The reduction mixture is filtered to remove the catalyst, and the filtrate is evaporated in vacuo to dryness to yield the reduction product as the residue. Preferably the hydrogenation is carried out in tetrahydrofuran since the starting materials are substantially soluble therein at room temperature.

The second step of the two-step cleavage portion of the procedure for preparing the 7-methoxy compounds of this invention involves the hydrolysis of the reduction intermediate under mildly acidic conditions.

The mildly acid cleavage can be carried out in solution or in the presence of silica gel (silicic acid in gel form). Accordingly, the intermediate reduction product is dissolved in an inert organic solvent such as ethyl acetate, acetonitrile, methylene chloride and the like, and the resulting mixture is vigorously stirred or shaken with a dilute aqueous mineral acid such as, for example, hydrochloric acid, sulphuric acid, or phosphoric acid, and the pH of the mixture is maintained between about pH 4 and pH 6. The resulting 7-amino-7-methoxy-3-cephem-3,4-dicarboxylic acid diester is recovered from the organic phase in a conventional manner.

Preferably, however, the mildly acidic cleavage of the intermediate reduction product is carried out in the presence of silica gel. According to this preferred mode of cleavage, the intermediate reduction product is dissolved in a suitable solvent, for example, a chlorinated hydrocarbon such as chloroform or methylene chloride, an ester, such as ethyl acetate, a ketone such as acetone or methyl isobutyl ketone; or an ether such as tetrahydrofuran or dioxane. The silica gel is then added to the resulting solution. The solution is stitrred for about two hours and is filtered. The silica gel then is washed on the filter, and the filtrate and washings are combined and evaporated in vacuo to dryness to yield the desired 7-amino-7-methoxy-3-cephem-3,4-dicarboxylic acid diester.

Representative of the 7-methoxy nucleus diesters of the present invention available by the hereinabove described techniques are:

tert-butyl 7-amino-7-methoxy-3-(4-methoxybenzyloxycarbonyl)-3-cephem-4-carboxylate,
benzhydryl 7-amino-7-methoxy-3-ethoxycarbonyl-3-cephem-4-carboxylate,
4'-methoxybenzyl 7-amino-7-methoxy-3-benzhydryloxycarbonyl-3-cephem-4-carboxylate,
benzhydryl 7-amino-7-methoxy-3-(4-methoxycarbonyl-3-cephem-4-carboxylate,
benzhydryl 7-amino-7-methoxy-3-(2-bromoethoxycarbonyl-3-cephem-4-carboxylate, and like compounds.

The 7-methoxy nucleus diesters can then be acylated by the conventional acylation procedures described hereinbefore. Generally, these procedures involve use of an activated form of the acid such as an acid halide, acid mixed anhydride, or an activated ester. Acylation of the 7-methoxy nucleus diesters provides the corresponding 7-acylamino-7-methoxy-3cephem-3,4-dicarboxylic acid diesters. Removal of either the C-4 carboxylic acid ester protecting group or both the C-4 and C-3 carboxylic acid protecting groups provides the biologically active 7-acylamino-7-methoxy-3-cephem compound of the formula

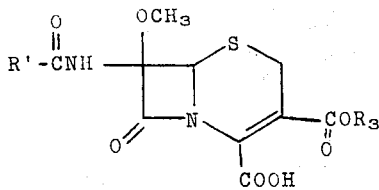

wherein R' and R₃ are as defined hereinabove. Exemplary of preferred 7-methoxycephem compounds of this invention are:

7-(2-thienylacetamido)-7-methoxy-3-methoxycarbonyl-3-cephem-4-carboxylic acid,
7-[D-(2-phenyl-2-formyloxyacetamido)]-7-methoxy-3-carboxy-3-cephem-4-carboxylic acid,
7-(2-phenyl-2-carboxyacetamido)-7-methoxy-3-(2-bromoethoxycarbonyl)-3-cephem-4-carboxylic acid,
7-(D-2-phenyl-2-aminoacetamido)-7-methoxy-3-ethoxycarbonyl-3-cephem-4-carboxylic acid,
7-[D-(2-phenyl-2-formyloxyacetamido)]-7-methoxy-3-methoxycarbonyl-3-cephem-4-carboxylic acid, and
7-(2-phenyl-2-carboxyacetamido)-7-methoxy-3-carboxy-3-cephem-4-carboxylic acid.

The free acids of this invention form carboxylate salts with any of a variety of inorganic and organic bases. Pharmaceutically acceptable carboxylate salts are formed by reacting the free acids with bases such as sodium hydroxide, sodium carbonate, potassium hydroxide, potassium 2-ethylhexanoate, calcium carbonate, ethylamine, 2-hydroxyethylamine and the like. Preferred carboxylate salt forms are the alkali metal salts. A preferred base for the formation of the potassium salt is potassium 2-ethylhexanoate. The carboxylate salts can be converted to the free acids by acidification. The free acids and their carboxylate salts can be considered as equivalent for the purposes of this invention.

The cephem antibiotics of this invention are relatively non-toxic substances which are useful in combatting infections in warm blooded mammals when administered parenterally in a pharmacuetically effective non-toxic dosage form. The 3-(substituted) carbonyl-3-cephem compounds can be formulated into liquid pharmaceutical form, e.g. in water, isotonic saline, or the like, and administered by intramuscular injections or by intravenous administration procedures to provide dosages of from about 125 mg. to 16 grams a day depending on the patient's body weight, the disease condition being treated, and other factors of concern to the patient's physician. In controlling infections in particular hosts, repeated administration of smaller doses may suffice, while in other instances larger non-toxic doses may be administered to achieve the desired control. The antibiotic compounds of this invention can be administered in the free acid form or in the form of a pharmaceutically acceptable non-toxic salt such as the sodium or potassium salt.

A highly preferred group of active compounds of the present invention are the compounds of the formula

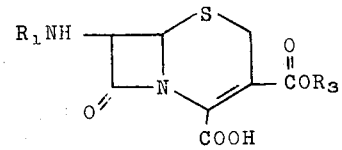

wherein $R_1$ is an acyl group of the formula

and $R_3$ is hydrogen, $C_1$-$C_6$ alkyl, or $C_1$-$C_6$ 2-haloalkyl.

A particularly preferred group of antibiotics are represented by the above formula wherein $R_3$ is $C_1$-$C_6$ alkyl or $C_1$-$C_6$ haloalkyl and R' is the group

wherein $R_{10}$ is phenyl or 4-hydroxyphenyl and W is hydroxy, formyloxy or carboxy. Illustrative of these preferred compounds are:

7-(D-mandelamido)-3-methoxycarbonyl-3-cephem-4-carboxylic acid,
7-(2-phenyl-2-carboxyacetamido)-3-ethoxycarbonyl-3-cephem-4-carboxylic acid,
7-[D-2-(4-hydroxyphenyl)-2-formyloxyacetamido)]-3-n-propoxycarbonyl-3-cephem-4-carboxylic acid,
7-[D-2-(4-hydroxyphenyl)-2-hydroxyacetamido)]-3-methoxycarbonyl-3-cephem-4-carboxylic acid,
7-(2-phenyl-2-carboxyacetamido)-3-cyclohexoxycarbonyl-3-cephem-4-carboxylic acid,
7-[D-(2-phenyl-2-formyloxyacetamido)]-3-isopropoxycarbonyl-3-cephem-4-carboxylic acid, and
7-(2-phenyl-2-carboxyacetamido)-3-methoxycarbonyl-3-cephem-4-carboxylic acid.

The following examples are provided to further illustrate this invention. It is not intended that this invention be limited in scope by reason of any of these examples.

PREPARATION 1

Benzhydryl 7-(2-thienylaceamido)-3-formyl-2-cephem-4-carboxylate

To a slurry of 7-(2-thienylacetamido-3-hydroxymethyl-2-cephem-4-carboxylic acid (23.6 g., 67 mmol.) in 500 ml. ethyl acetate was added dropwise a solution of diphenyldiazomethane (19.4 g., 0.1 mole) in 50 ml. ethyl acetate. The reaction mixture was refluxed for 15 minutes, cooled to room temperature and evaporated in vacuo to dryness. The residue was washed with 1 liter of 1:1-ethyl ether:petroleum ether giving a pink solid: benzhydryl 7-(2-thienylacetamido)-3-hydroxymethyl-2-cephem-4-carboxylate (33 g., 94.2% yield).

To a stirred solution of the benzhydryl ester in 1 liter of acetone was added dropwise 33.6 ml. (76 mmol., 1.2 eq.) of chromic acid. The reaction mixture was allowed to stir at room temperature for 8 minutes. Isopropyl alcohol (35 ml.) was then added, and the mixture was stirred for an additional 5 minutes. The reaction mixture was evaporated in vacuo to low volume and extracted with ethyl acetate (2 × 400 ml.). The organic extracts were combined and washed successively with water (4X), sodium bicarbonate solution, water, 1N.HCl, and sodium chloride solution, and then dried ($Na_2SO_4$). Evaporation in vacuo to dryness gave 31.1 g. (95.4%) of crude benzhydryl 7-(2-thienylacetamido)-3-formyl-2-cephem-4-carboxylate which was purified either by crystallization from toluene (43% yield) or by chromatography on silica gel (50 g.) using a benzene-ethyl acetate gradient (22 g., 62% yield). The product was recrystallized from methylene chloride-hexane to give white needles (mp 149°–150° C.): ir ($CHCl_3$) 1785 ($\beta$-lactam C = 0), 1680 (amide C = 0) and 2830 $cm^{-1}$ (formyl C = 0); nmr ($CDCl_3$) 3.80 (s, 2, side chain $CH_2$), 5.12 (d, 1, J = 4.0 Hz, $C_6$-H), 5.40 (q, 1, J = 4.0 and 8.0 Hz, $C_7$-H), 5.51 (s, 1, $C_4$-H), and 9.20 ppm (s, 1, CHO).

Analysis Calcd. for $CH_{27}H_{22}N_2O_5S_2$: C, 62.53; H, 4.28; N, 5.40; Found: C, 62.33; H, 4.19; N, 5.17

PREPARATION 2

Benzhydryl 7-(2-thienylacetamido)-3-(1,3-dioxolan-2-yl)-2-cephem-4-carboxylate Benzhydryl 7-(2-thienylacetamido)-3-formyl-2-cephem-4-carboxylate (21.5 g., 41.5 mmol.) was combined with 11.6 ml. of ethylene glycol (0.2 mole) and toluenesulfonic acid monohydrate (0.197 g., 1.04 mmol.) in 500 ml. benzene. The mixture was refluxed for 10 hours using a Dean-Stark trap (1.5 ml. water collected), cooled, and evaporated in vacuo to dryness. The product was taken up in ethyl acetate and washed successively with sodium bicarbonate solution (2X), water (2X) and sodium chloride solution and subsequently dried over $Na_2SO_4$. Evaporation in vacuo to dryness gave a product which was chromatographed on 40 g. of silica gel using a benzene-ethyl acetate gradient. Crystallization of the purified product from methylene chloride-hexane gave benzhydryl 7(2-thienylacetamido)-3-(1,3-dioxolan-2-yl)-2-cephem-4-carboxylate as colorless needles (15.07 g., 64.2%): mp 142°–143°; ir ($CHCl_3$) 1780 $cm^{-1}$ ($\beta$-lactam C = 0); nmr ($CDCl_3$) 3.3–3.9 (m, 4, $-CH_2-CH_2-$), 3.83 (s, 2, side chain $CH_2$), 5.10 (d, 1, J = 4.0 Hz, $C_6$-H), 5.17 (s, 1, acetal CH), 5.21 (s, 1, $C_4$-H) and 5.45 ppm (q, 1, J = 4.0 and 8.0 Hz, $C_7$-H).

Analysis Calcd. for $C_{29}H_{26}O_6S_2$: C, 61.69; H, 4.66; N, 4.98; Found: C, 61.69; H, 4.43; N, 5.10

PREPARATION 3

Methyl 7-(2-thienylacetamido)-3-(1,3-dioxolan-2-yl)-2-cephem-4-carboxylate

A solution of chromic acid (3.39 ml., 15 mmol.) was added dropwise to a cooled solution of 7-(2-thienylacetamido)-3-hydroxymethyl-2-cephem-4-carboxylic acid (3.54 g., 10 mmol.) and 260 ml. of acetone. The mixture was allowed to react with cooling for 6 minutes after which time was added 3 ml. of isopropyl alcohol and 300 ml. of ethyl acetate. The mixture was then washed with water (4X), and brine, and dried (sodium sulfate). Evaporation of the resulting solution to dryness gave 2.83 g. (81%) of a pale yellow froth. This product was dissolved in ethyl acetate and treated with excess diazomethane. The excess diazomethane was destroyed with acetic acid, and the reaction mixture was washed with sodium bicarbonate solution (2X), and brine, and dried over sodium sulfate. Evaporation in vacuo to dryness gave 2.085 g. of a froth. This product was combined with ethylene glycol (11.2 ml., 0.2 mole) and toluene sulfonic acid monohydrate (0.475 g., 2.5 mmol.) in 100 ml. of benzene. The resulting mixture was refluxed using a Dean-Stark trap for 1.5 hours. Ethyl acetate was then added to the reaction mixture, and the solution as then washed successively with water (4X), sodium bicarbonate solution, and brine and dried over anhydrous sodium sulfate. Evaporation in vacuo to dryness gave 1.9 g. of a yellow froth which was chromatographed on silica gel using a benzene-ethylene acetate gradient to give 0.975 g. (24%) of methyl 7-(2-thienylacetamido)-3-(1,3-dioxolan-2-yl)-2-cephem-4-carboxylate as white crystals. Recrystallization from acetone/hexane gave white needles (mp 169°–170° C): nmr ($CDCl_3$) 3.75 (s, 3, $CO_2CH_3$), 3.84 (s, 2, side chain $CH_2$), 3.88 (broad s, 4, 0-$CH_2CH_2$-), 5.06 (s, 1), 5.20 (d, 1, J = 4.0 Hz, $C_6$—H), 5.30 (s, 1), 5.36 (q, J = 4.0 and 8.0 Hz, $C_7$—H) and 6.58 ppm (s,1, $C_2$ —H).

Analysis Calcd. for $C_{17}H_{18}N_2O_6S_2$: C, 49.75; H, 4.42; N, 6.82; Found: C, 49.63; H, 4.69; N, 6.62.

EXAMPLE 1

Benzhydryl 7-(2-thienylacetamido)-3-(2-bromoethoxycarbonyl)-2-cephem-4-carboxylate Benzhydryl 7-(2-thienylacetamido)-3-(1,3-dioxolan-2-yl)-2-cephem-4-carboxylate (15.07 g., 26.8 mmol.) was combined with N-bromosuccinimide (5.25 g., 29.5 mmol.) and azobisisobutyronitrile (37.5 mg., 0.26 mmol., .01 eq.) in 1200 ml. of benzene. The mixture was gently refluxed for 20 minutes, cooled, and evaporated in vacuo to dryness to give a dark colored product. Chromatography on 30 g. of silica gel using a toluene-ethyl acetate gradient provided 7.61 g. (44.4%) of benzhydryl 7-(2-thienylacetamido)-3-(2-bromoethoxycarbonyl)-2-cephem-4-carboxylate: mp 129°–130°; ir ($CHCl_3$) 1785 $cm^{-1}$ ($\beta$-lactam C = 0); nmr ($CDCl_3$) 3.25 (t, 2, J =0 Hz, $CH_2Br$), 3.83 (s, 2, side chain $CH_2$), 4.30 (t, 2, J = 6.0 Hz, O—$CH_2$—), 4.95 (d 1, J = 4.0 Hz, $C_6$—H), 5.45 (q, 1, J = 4.0 and 8.0 Hz, $C_7$—H), 5.50 (s, 1, $C_4$-H) and 7.80 ppm (s, 1, $C_2$—H).

Analysis Calcd. for $C_{29}H_{25}BrN_2O_6S_2$: C, 54.29; N, 3.93; N, 4.37; Found: C, 54.22; H, 3.90; N, 4.27

EXAMPLE 2

Benzhydryl 7-(2-thienylacetamido)-3-(2-iodoethoxycarbonyl)-2-cephem-4-carboxylate Benzhydryl 7-(2-thienylacetamido)-3-(2-bromoethoxycarbonyl)-2-cephem-4-carboxylate (7.61 g., 12 mmol.) was combined with sodium iodide (6.75 g., 45 meq.) in 100 ml. acetone. The reaction mixture was degassed and then heated to 35° with stirring for 16 hours. The reaction mixture was filtered and evaporated to dryness. The residue was dissolved in ethyl acetate and washed with water (3X) and brine and dried ($Na_2SO_4$). Evaporation in vacuo to dryness provided 7.78 g. (95.5%) of benzhydryl 7-(2-thienylacetamido)-3-(2-iodoethoxycarbonyl)-2-cephem-4-carboxylate: ir ($CHCl_3$) 1785 cm$^{-1}$ ($\beta$-lactam C = 0); nmr ($CDCl_3$) 2.96 (t, 2, J = 7.0 Hz, $CH_2I$), 3.80 (s, 2, side chain $CH_2$), 4.24 (t, 2, J = 7.0 Hz, —$OCH_2$—), 4.95 (d, 1 J = 4.0 Hz, $C_6$—H), 5.24 (q, 1, J = 4.0 Hz, $C_7$—H, rest of the signal covered by $C_4$—H), 5.50 (s, 1, $C_4H$), and 7.80 ppm (s, 1, $C_2$-H).

EXAMPLE 3

Benzhydryl 7-(2-thienylacetamido)-3-(2-bromoethoxycarbonyl)-3-cephem-4-carboxylate To a cooled (5° C.) stirred solution of benzhydryl 7-(2-thienylacetamido)-3-(2-bromoethoxycarbonyl)-2-cephem-4-carboxylate (0.29 g., 0.453 mmol.) in 30 ml. chloroform was added 85% m-chloroperbenzoic acid (0.101 g., 497 mmol.) in 3 ml. chloroform. The mixture was allowed to stir with cooling for 30 minutes, and then was washed with sodium bicarbonate solution (2X) and sodium chloride solution and dried over $Na_2SO_4$. Evaporation in vacuo gave 301 mg. of the $\Delta^3$ sulfoxide. The sulfoxide was dissolved in 25 ml. dimethylformamide, cooled briefly, and then treated with 0.06 ml. (0.678 mmol., 1.5 eq.) phosphorous trichloride. The mixture was allowed to stir at ambient temperature for 30 minutes. Ethyl acetate was added to the reaction mixture, and then it was washed successively with water (2X), aqueous sodium bicarbonate (2X), and brine. The organic layer was dried over anhydrous $Na_2SO_4$ and evaporated in vacuo to dryness. The crude product was chromatographed on 5 g. of silica gel using a benzene-ethyl acetate gradient providing benzhydryl 7-(2-thienylacetamido)-3-(2-bromoethoxycarbonyl)-3-cephem-4-carboxylate (0.154 g., 53%) as a colorless solid: ir ($CHCl_3$) 1799 cm$^{-1}$ ($\beta$-lactam C = 0); nmr (DMSO-$d_6$) 3.34 (m, 2, $CH_2Br$), 3.76 (s, 2, side chain $CH_2$), 3.8–4.4 (m), 5.20 (d, 1, J = 5.0 Hz, $C_6$—H) and 5.86 ppm (q, 1, J = 5.0 and 9.0 Hz, $C_7$—H).

EXAMPLE 4

7-(2-thienylacetamido)-3-(2-bromoethoxycarbonyl)-3-cephem-4-carboxylic acid

To a cold solution of benzhydryl 7-(2-thienylacetyl)-3-(2-bromoethoxycarbonyl)-3-cephem-4-carboxylate (81 mg., 0.126 mmol.) in 1 ml. of anisole was added 3 ml. of trifluoroacetic acid. The mixture was allowed to stir without cooling for 6 minutes. n-Heptane (50 ml.) was added and the total volume of the resulting mixture was reduced in vacuo to ca. 8 ml. Addition of 5 ml. of n-heptane to the residue precipitated an off-white solid which was filtered. This precipiate was dissolved in acetone and the resulting solution evaporated to low volume. The residue was transferred to a separatory funnel with the aid of ethyl acetate and extracted twice with aqueous sodium bicarbonate. The aqueous extracts were combined and layered with ethyl acetate and acidified with 1N.HCl. The organic layer was separated, washed with brine, dried over anhydrous $Na_2SO_4$, and evaporated in vacuo to dryness to give 7-(2-thienylacetamido)-3-(2-bromoethoxycarbonyl)-3-cephem-4-carboxylic acid as a white solid (51 mg., 85%).

EXAMPLE 5

Benzhydryl 7-(2-thienylacetamido)-3-(2-iodoethoxycarbonyl)-3-cephem-4-carboxylate, 1-oxide To a cooled (ice bath 10 minutes), stirred solution of benzhydryl 7-(2-thienylacetamido)-3-(2-iodoethoxycarbonyl)-2-cephem-4-carboxylate (980 mg., 1.42 mmol.) in 70 ml. chloroform was added dropwise a solution of 85% m-chloroperbenzoic acid (0.319 g., 1.56 mmol.) in 5 ml. of chloroform. The mixture was allowed to stir overnight (11 hours) warming slowly to room temperature. The reaction mixture was washed successively with aqueous sodium bicarbonate (3X), water, and brine, dried over $Na_2SO_4$, and evaporated in vacuo to dryness. Chromatography on 5 g. of silica gel using a toluene-ethyl acetate gradient provided 0.219 g. of the starting material and 0.314 g. of benzhydryl 7-(2-thienylacetamido)-3-(2-iodoethoxycarbonyl)-3-cephem-4-carboxylate, 1-oxide (42% yield, corrected): nmr (DMSO-$d_6$) 3.03 (m,$CH_2I$), 3.8–4.3 (m, amide side chain $CH_2$, —$OCH_2$—, and $C_2$—H), 5.05 (d, J = 4.0 Hz, $C_6$—H) and 6.04 ppm (q, 1, J = 4.0 and 8.0 Hz, $C_7$—H).

EXAMPLE 6

Benzhydryl 7-(2-thienylacetamido)-3-(2-iodoethoxycarbonyl)-3-cephem-4-carboxylate To a cooled (ice bath 5 minutes), stirred solution of benzhydryl 7-(2-thienylacetamido)-3-(2-iodoethoxycarbonyl)-3-cephem-4-carboxylate, 1-oxide (0.314 g., 0.445 mmol.) in 20 ml. dimethylformamide was added 0.116 ml. phosphorous trichloride (1.34 mmol., 3.0 eq.). The ice bath was removed and the solution was stirred at room temperature for 45 minutes. Ethyl acetate was added to the reaction mixture, and the resulting mixture was washed with sodium bicarbonate solution (2X), water and brine and then dried over anhydrous $Na_2SO_4$. Evaporation of the solvent in vacuo provided a product which was subsequently chromatographed on silica using a toluene-ethyl acetate gradient to give benzhydryl 7-(2-thienylacetamido)-3-(2-iodoethoxycarbonyl)-3-cephem-4-carboxylate (0.207 g., 68%): nmr (DMSO-$d_6$) 3.0 (t, $CH_2$—I), 3.80 (s, 2, side chain $CH_2$), 3.6–4.2 (m, O—$CH_2$—), 5.25 ppm (d, 1, J = 5.0, $C_6$—H), and 5.80 (q, 1, J = 5.0 and 8.0 Hz, $C_7$—H).

EXAMPLE 7

Benzhydryl 7-(2-thienylacetamido)-3-carboxy-2-cephem-4-carboxylate

Benzhydryl 7-(2-thienylacetamido-3-(2-iodoethoxycarbonyl)-2-cephem-4-carboxylate (2.79 g., 4.05 mmol.) was dissolved in a mixture of 8 ml. glacial acetic acid and 48 ml. dimethylformamide at 0° and was reacted with 2.79 g. zinc dust (10.5 eq.) for 1.5 hours. The reaction mixture was diluted with ethyl acetate and filtered through a celite filter. The filtrate was washed successively with sodium bicarbonate solution (3X), water, 1N.HCl, and brine and then dried ($Na_2SO_4$). Evaporation to dryness in vacuo gave 1.92 (89%) of benzhydryl 7-(2-thienylacetamido)-3-carboxy-2-cephem-4-carboxylate: nmr ($CDCl_3$) 3.84 (s, side chain $CH_2$), 4.99 (d, 1, J = 4.0 Hz, $C_6$—H), 5.45 (m, $C_4$—H and $C_7$—H), and 7.80 ppm (s, $C_2$—H).

EXAMPLE 8

Benzhydryl 7-(2-thienylacetamido)-3-methoxycarbonyl-2-cephem-4-carboxylate.

A solution diazomethane (0.68 g., 16.2 mmol.) in ethyl acetate was added dropwise to a stirred, cooled (ca. 5° C.) solution of benzhydryl 7-(2-thienylacetamido)-3-carboxy-2-cephem-4-carboxylate (5.80 g., 10.8 mmol.) in 250 ml. ethyl acetate. After 30 minutes the excess diazomethane was destroyed with acetic acid. The reaction mixture was washed with sodium bicarbonate solution, water and brine and then was dried over anhydrous $Na_2SO_4$. Evaporation in vacuo of the ethyl acetate solution gave 5.72 g. (96.3%) of benzhydryl 7-(2-thienylacetamido)-3-methoxycarbonyl-2-cephem-4-carboxylate (tlc-single spot): nmr ($CDCl_3$) 3.67 (s, $CO_2CH_3$), 3.84 (s, side chain $CH_2$), 5.00 (d, J = 4.0 Hz, $C_6$—H), 5.00 (m, J = 4.0 and 8.0 Hz, $C_7$—H) and 7.66 ppm (s, $C_2$—H).

EXAMPLE 9

Benzhydryl 7-(2-thienylacetamido)-3-methoxycarbonyl-3-cephem-4-carboxylate.

A solution of m-chloroperbenzoic acid (2.34 g., 11.5 mmol.) in 40 ml. chloroform was added dropwise over a 15 minute period to a cooled (ice bath 10 minutes), stirred solution of the benzhydryl 7-(2-thienylacetamido)-3-methoxycarbonyl-2-cephem-4-carboxylate (5.72 g., 10.25 mmol.) in 250 ml. chloroform. After two hours the reaction mixture was washed with sodium bicarbonate solution (3X) and brine, dried ($Na_2SO_4$), and evaporated in vacuo to dryness to give the corresponding 3-cephem sulfoxide (tlc - single spot). The product sulfoxide was dissolved in 100 ml. dimethylformamide (cooled in ice bath) and was treated with 1.37 ml. phosphorous trichloride (15.7 mmol., 1.5 eq.). The mixture was removed from the ice bath and allowed to react at room temperature for 45 minutes. Ethyl acetate was added to the reaction mixture, and the resulting solution was washed successively with sodium bicarbonate solution (3X), water (2X), and brine. After drying over anhydrous $Na_2SO_4$ the solution was evaporated in vacuo to dryness. The crude product was chromatographed on 10 g. silica gel using a toluene-ethyl acetate gradient to provide 3.82 g. (66.8%) of benzhydryl 7-2-thienylacetamido)-3-methoxycarbonyl-3-cephem-4-carboxylate as a yellow solid: mp 201° decomp (methylene chloride-hexane); uv max (EtOH) 283 m$\mu$ ($\epsilon$ 13.6 × 10$^3$), shoulder at 243 m$\mu$; ir ($CHCl_3$) 1798 cm$^{-1}$ ($\beta$-lactam C = 0); nmr (DMSO-$d_6$) 3.30 (s, 3, $CO_2CH_3$), 3.74, 3.80 (m, 4, side chain $CH_2$, $C_2$—H), 5.25 (d, 1 J = 5.0 Hz, $C_6$—H), 5.90 (q, 1, J = 4.0 and 8.0 Hz, $C_7$—H) and 7.0, 7.4 ppm (m, 13, benzhydryl ester, thienyl).

EXAMPLE 10

7-(2-thienylacetamido)-3-methoxycarbonyl-3-cephem-4-carboxylic acid

To a cooled (5° C.) slurry of benzhydryl 7-(2-thienylacetamido)-3-methoxycarbonyl-3-cephem-4-carboxylate (0.316 g., 0.579 mmol.) in 5 ml. anisole was added 5.0 ml. of cold trifluoroacetic acid. The solid immediately dissolved and the resulting colorless solution was stirred with cooling for 10 minutes after which time 50 ml. n-heptane was added. The resulting solution was evaporated in vacuo to a low volume causing the precipitation of a white solid. This solid was filtered and subsequently dissolved in acetone. The acetone solution was evaporated in vacuo to dryness. The residue was dissolved in ethyl acetate, and the resulting solution was extracted three times with cold sodium bicarbonate solution. The aqueous extracts were combined, layered with ethyl acetate and acidified with 1N.HCl. The organic layer was separated, washed with brine, and dried ($Na_2SO_4$). Evaporation in vacuo to dryness gave 0.214 g. (97%) of 7-(2-thienylacetamido)-3-methoxycarbonyl-3-cephem-4-carboxylic acid.

EXAMPLE 11

Benzhydryl 7-(2-thienylacetamido)-3-isopropoxycarbonyl-2-cephem-4-carboxylate.

Isopropyl iodide (0.65 ml., 6.5 mmol.) was added to a solution of benzhydryl 7-(2-thienylacetamido)-3-carboxylic acid 2-cephem-4-carboxylate, sodium salt (0.725 g., 1.30 mmol.) in 3.0 ml. of hexamethylphosphoramide (HMPA). The mixture was allowed to stir at room temperature for 37 hours, and then transferred with the aid of ethyl acetate to a separatory funnel. The solution was washed successively with 1N. HCl(3X) and brine (2X) and then was dried over anhydrous sodium sulfate. Evaporation in vacuo to dryness gave a product which was chromatographed on 5 g. of silica gel using a toluene-ethyl acetate gradient to give 522 mg. (70%) of the isopropyl ester as a white froth: ir ($CHCl_3$) 1790 cm$^{-1}$ ($\beta$-lactam); nmr ($CDCl_3$) 1.14 (2 overlapping doublets, 6, —CH $(CH_3)_2$), 3.84 (s, 2, side chain $CH_2$), 5.00 (m, 2, $C_6$—H and —CH$(CH_3)_2$), 5.45 (q, 1, J = 4.0 and 8.0 Hz, $C_7$—H), 5.55 (m, 1, $C_4$—H), 6.9–7.5 (m, benzhydryl ArH and thienyl), and 7.72 (m, 1, $C_2$—H). This product was isomerized to the corresponding 3-cephem by the procedures described in Example 9.

EXAMPLE 12

7-thienylacetamido-3-(isopropoxycarbonyl)-3-cephem-4-carboxylic acid.

Benzhydryl 7-thienylacetamido-3-isopropoxycarbonyl)-3-cephem-4-carboxylate was deesterified (83%) with a trifluoroacetic acid-anisole mixture as described in Example 10 to give the title acid as a white solid. The product exhibitied biological activity against both gram-positive and gram-negative organisms.

EXAMPLE 13

Benzhydryl 7-thienylacetamido-3-(n-propoxycarbonyl)-2-cephem-4-carboxylate

The same procedure was followed as described in Example 11 using benzhydryl 7-thienylacetamido-3-carboxylic acid-2-cephem-4-carboxylate sodium salt and n-propyl iodide as the starting materials. The title diester was isolated by chromatography on silica gel in 75% yield: ir ($CHCl_3$) 1790 $cm^{-1}$ ($\beta$-lactam C = 0); nmr ($CDCl_3$) 0.71 (m, 3, $CH_3$), 1.30 (m, 2, $OCH_2CH_2CH_3$), 3.71 (s, 2, side chain —$CH_2$—), 3.90 (m, 2, $OCH_2CH_2CH_3$), 4.86 (d, 1, J = 4.0 Hz, $C_6$—H), 5.35 (q, 1, J = 4.0 Hz and 8.0 Hz, $C_7$—H), 5.44 (d, 1, J = 1.0 Hz, $C_4$—H), and 7.65 ppm (d, 1, J = 1.0 Hz, $C_2$—H).

EXAMPLE 14

Benzhydryl 7-thienylacetamido-3-(n-propoxycarbonyl)-3-cephem-4-carboxylate.

To a cooled (5° C.) stirred solution of 0.561 g. benzhydryl 7-thienylacetamido-3-(n-propoxycarbonyl)-2-cephem-4-carboxylate in 60 ml. chloroform was added a solution of 0.218 g. of m-chloroperbenzoic acid in 2 ml. chloroform. After 12.5 hours, during which time the mixture was allowed to warm to room temperature, the reaction mixture was washed with sodium bicarbonate solution (2×) and brine and then dried ($Na_2SO_4$). Evaporation to dryness gave a product which was chromatographed on 5.0 g. of silica gel. The purified product thereby obtained was dissolved in 25 ml. dimethylformamide. The solution was cooled in an ice bath and 0.214 ml. of $PCl_3$ was added. The reaction mixture was allowed to stir without cooling for 1 hour and was then transferred to a separatory funnel with the aid of ethyl acetate. The mixture was washed successively with sodium bicarbonate solution (2×), water (4×), and brine (2×) and then dried over anhydrous sodium sulfate. Evaporation in vacuo to dryness gave a product which was chromatographed on 5.0 g. of silica gel using a toluene-ethyl acetate gradient to give 0.328 g. (58%) of benzhydryl 7-thienylacetamido-3-(n-propoxycarbonyl)-3-cephem-4-carboxylate as a pale yellow solid: ir ($CHCl_3$) 1800 $cm^{-1}$ ($\beta$-lactam C = 0); nmr ($CDCl_3$) 0.65 (m, 3, —$CH_2CH_2CH_3$), 1.18 (m, 2, —$OCH_2CH_2CH_3$), 3.68 (s, 2, side chain $CH_2$), 3.68 (m, 4, —$OCH_2CH_2CH_3$ and $C_2$—H), 4.85 (d, 1, J = 5.0 Hz, $C_6$—H) and 5.82 ppm (q, 1, J = 5.0 and 9.0 Hz, $C_7$—H.).

EXAMPLE 15

7-Thienylacetamido-3-(n-propoxycarbonyl)-3-cephem-4-carboxylic acid.

Benzhydryl 7-thienylacetamido- 3-(n-propoxycarbonyl)-3-cephem-4-carboxylate was deesterified (65%) with a trifluoroacetic acid-anisole mixture as described in Example 10 to give the title acid as a white solid. The product exhibitied biological activity against both gram-positive and gram-negative organisms.

EXAMPLE 16

Benzhydryl 7-(2-thienylacetamido)-3-(4-nitrobenzyloxycarbonyl)-2-cephem-4-carboxylate.

To a stirred solution of benzhydryl 7-(2-thienylacetamido)-3-carboxy-2-cephem-4-carboxylate (1.604 g., 3 mmol.) in 175 ml. of ethyl acetate was added dropwise 65 ml. of 4-nitrophenyldiazomethane solution (0.013 g./ml., 5.18 mmol.). The reaction mixture was allowed to stir at room temperature for 48 hours and then evaporated in vacuo to dryness. The product was chromatographed on silica gel using a toluene-ethyl acetate gradient to provide 1.66 g. (83%) of benzhydryl 7-(2-thienylacetamido)-3-(4-nitrobenzyloxycarbonyl)-2-cephem-4-carboxylate as a yellow froth: ir ($CHCl_3$) 1788 $cm^{-1}$ ($\beta$-lactam C = 0); nmr ($CDCl_3$) 3.82 (s, 2, side chain $CH_2$), 4.95 (d, 1, J = 4.0 Hz, $C_6$—H), 5.12 (s, 2, nitrobenzyl $CH_2$), 5.45 (q, 1, J = 4.0 and 8.0 Hz, $C_7$—H), 5.50 (s, 1, $C_4$-H) 7.80 (s, 1, $C_2$—H) and 6.9, 7.3 ppm (ArH).

EXAMPLE 17

Benzhydryl 7-(2-thienylacetamido-3-(4-nitrobenzyloxycarbonyl)-3-cephem-4-carboxylate.

The same procedure was followed as described in Example 14 except benzhydryl 7-(2-thienylacetamido)-3-(4-nitrobenzyloxy-carbonyl)-2-cephem-4-carboxylate was used as the starting material instead of the corresponding methoxycarbonyl compound. The product 3-cephem compound was isolated in 48% yield and was crystallized from a mixture of methylene chloride, acetone and hexane to give pale yellow needles (mp 165°–166° C.): ir ($CHCl_3$) 1801 $cm^{-1}$ ($\beta$-lactam C = 0); nmr ($CDCl_3$) 3.42, 3.86 (ABq, 2, J = 18.0 Hz, $C_2$—H), 3.80 (s, 2, side chain $CH_2$), 4.54, 4.94 (ABq, 2, J = 12.0 Hz, nitrobenzyl $CH_2$), 4.95 (d, 1, J = 5.0 Hz, $C_6$—H), 5.85 (q, 1, J = 5.0 and 9.0 Hz, $C_7$—H) and 7.0, 7.2 ppm (ArH).

Analysis Calcd. for $C_{34}H_{27}N_3O_8S_2$: C, 60.98; H, 4.06; N, 6.27; Found: C, 61.20; H, 4.24; N, 6.33.

EXAMPLE 18

Methyl 7-(2-thienylacetamido)-3-(2-bromoethoxycarbonyl)-2-cephem-4-carboxylate.

The same procedure was followed as described in Example 1 except that methyl 7-(2-thienylacetamido)-3-(1,3-dioxolan-2-yl)-2-cephem-4-carboxylate was used as the starting material instead of the corresponding benzhydryl ester to give the product in 42–60% yield. An nmr spectrum ($CDCl_3$) exhibited the following signals:

3.53 (m, 2, $CH_2$—Br), 3.80 (s, 3, $CO_2Me$), 3.86 (s, 2, side chain $CH_2$), 4.50 (m, 2, $CO_2CH_2$), 5.26 (d, 1, J = 4.0 Hz, $C_6$—H), 5.40 (s, 1, $C_4$—H), 5.57 (q, 1, J = 4.0 and 8.0 Hz, $C_7$—H), and 7.80 ppm (s, 1, $C_2$—H).

EXAMPLE 19

Methyl 7-(2-thienylacetamido)-3-(2-iodoethoxycarbonyl)-2-cephem-4-carboxylate.

The same procedure was followed as described in Example 2 except that methyl 7-(2-thienylacetamido)-3-(2-bromoethoxycarbonyl)-2-cephem-4-carboxylate was used as the starting material instead of the corresponding benzhydryl ester giving the product in 93.5% yield. The product exhibited the following nmr signals (CDCl$_3$):
3.30 ($m$, 2, CH$_2$—I), 3.76 ($s$, 3, CO$_2$CH$_3$), 3.80 ($s$, 2, side chain CH$_2$), 4.40 ($m$, 2, CO$_2$CH$_2$—), 5.10 ($d$, 1, J = 4.0 Hz, C$_6$—H), 5.22 ($s$, 1, C$_4$—H), 5.50 ($q$, J = 4.0 and 8.0 Hz, C$_7$—H) and 7.80 ppm ($s$, 1, C$_2$—H).

EXAMPLE 20

Methyl 7-(2-thienylacetamido)-3-benzhydryloxycarbonyl-2-cephem-4-carboxylate.

Zinc dust (1.573 g., 24 mmol.) was added to a cooled (approximately 5° C.), stirred solution of methyl 7-(2-thienylacetamido)-3-(2-iodoethoxycarbonyl)-2-cephem-4-carboxylate (1.573 g., 2.93 mmol.) in a mixture of 5 ml. of glacial acetic acid and 30 ml. of dimethylformamide. The reaction mixture was allowed to stir with cooling for 1.5 hours after which time ethyl acetate was added. The resulting mixture was filtered through a celite filter. The filtrate was washed successively with sodium bicarbonate solution (3×), 1N.HCl, and brine and dried over anhydrous sodium sulfate. Evaporation of the filtrate to dryness gave 1.305 g. of a product which was then dissolved in ethyl acetate and treated with excess diphenyldiazomethane. The mixture was refluxed for ten minutes and cooled to room temperature. Evaporation of the reaction mixture to dryness gave a product which was chromatograhed on silica gel using a benzene-ethyl acetate gradient to give 0.842 g. (52.5%) of methyl 7-(2-thienylacetamido)-3-benzhydryloxycarbonyl-2-cephem-4-carboxylate: nmr 3.58 ($s$ 3, CO$_2$CH$_3$), 3.78 ($s$, 2, side chain CH$_2$), 5.08 ($d$, 1, J = 4.0 Hz, C$_6$—H), 5.42 ($s$, 1, C$_4$—H), 5.57 ($q$, 1, J = 4.0 and 8.0 Hz, C$_7$—H) and 7.75 ppm ($s$, 1, C$_2$—H).

EXAMPLE 21

Methyl 7-(2-thienylacetamido)-3-benzhydryloxycarbonyl-3-cephem-4-carboxylate.

The same oxidation-reduction procedure was followed as described in Example 3. The corresponding 2-cephem was used as the starting material. The product (62%) was crystallized from methylene chloride-hexane to give white needles (mp 163°–164° C.): ir (CHCl$_3$) 1798 cm$^{-1}$ ($\beta$-lactam C = 0); nmr (CDCl$_3$) 3.45, 3.87 (ABq, 2, J = 18.0 Hz, C$_2$—H) 3.53 ($s$, 3, CO$_2$CH$_3$), 3.85 ($s$, 2, side chain CH$_2$), 5.00 ($d$, 1, J = 4.0 Hz, C$_6$—H), and 5.85 ppm ($q$, 1, J = 4.0 and 8.0 Hz, C$_7$—H).

Analysis Calcd. for C$_{28}$H$_{24}$N$_2$O$_6$S$_2$: C, 61.30; H, 4.41; N, 5.11; Found: C, 61.07; H, 4.33; N, 4.86.

EXAMPLE 22

Methyl 7-(2-thienylacetamido)-3-carboxy-3-cephem-4-carboxylate.

Cold trifluoroacetic acid (5 ml.) was added with stirring to a cold solution of methyl 7-(2-thienylacetamido)-3-benzhydryloxycarbonyl)-3-cephem-4-carboxylate (260 mg., 0.475 mmol.) and 5 ml. of anisole. After stirring for 10 minutes with cooling 50 ml. of n-heptane was added to the reaction mixture. Evaporation to a low volume in vacuo gave a precipitate which was filtered and then dissolved in acetone. This solution was filtered and evaporated to dryness. The residue was dissolved in cold ethyl acetate, and the resulting solution was extracted with cold sodium bicarbonate solution (3×). The aqueous extracts were combined, layered with cold ethyl acetate, and acidified with cold 1N.HCl. The ethyl acetate layer was separated, washed with water, and brine, and dried (Na$_2$SO$_4$). Evaporation in vacuo to dryness provided 176 mg. (97%) of a pale yellow solid identified as methyl 7-(2-thienylacetamido)-3-carboxy-3-cephem-4-carboxylate: nmr (acetone d-6) 3.73 ($s$, 3, CO$_2$CH$_3$), 3.90 ($s$, 2, side chain CH$_2$), ca. 3.9 ($m$, 2, center of AB at C$_2$), 5.20 ($d$, 1, J = 4.0 Hz, C$_6$—H), and 5.91 ppm ($q$, J = 4.0 and 8.0 Hz, C$_7$—H).

EXAMPLE 23

Benzhydryl 7-(2-thienylacetamido)-3-benzhydryloxycarbonyl-2-cephem-4-carboxylate.

Zinc dust (1.60 g.) was added to a cooled, stirred solution of benzhydryl 7-(2-thienylacetamido)-3-(2-iodoethoxycarbonyl)-2-cephem-4-carboxylate (1.60 g., 2.33 mmol.) in a mixture of 5 ml. of glacial acetic acid and 30 ml. of dimethylformamide. The mixture was allowed to cool with stirring for 1.5 hours after which time the reaction mixture was diluted with ethyl acetate and filtered through a celite filter. The filtrate was then washed successively with sodium bicarbonate solution (3×), 1N.HCl, and brine, and dried over anhydrous sodium sulfate. Excess diphenyldiazomethane was added and the mixture was refluxed gently for 10 minutes. Evaporation to dryness gave a residue which was chromatographed on a silica gel column using a benzene-ethyl acetate gradient to give 1.289 g. (79%) of benzhydryl 7-(2-thienylacetamido)-3-benzhydryloxycarbonyl-2-cephem-4-carboxylate: ir (CHCl$_3$) 1785 cm$^{-1}$ ($\beta$-lactam C = 0); nmr (CDCl$_3$) 3.90 ($s$, 2, side chain CH$_2$), 4.94 ($d$, J = 4.0 Hz, 1, C$_6$—H), 5.41 ($q$, 1, J = 4.0 and 8.0 Hz), 5.59 ($s$, 1, C$_4$—H), and 7.80 ppm ($s$, 1, C$_2$—H).

EXAMPLE 24

Benzhydryl 7-(2-thienylacetamido)-3-benzhydryloxycarbonyl-3-cephem-4-carboxylate.

The same oxidation-reduction procedure was followed as described in Example 9. Chromatograhy of the crude product on silica gel using a benzene-ethyl acetate gradient provided 15.2% of the starting 2-cephem compound ahd 61.6% yield of the 3-cephem dibenzhydryl ester: ir (CHCl$_3$) 1799 cm$^{-1}$ ($\beta$-lactam C = 0); nmr (CDCl$_3$) 3.33, 3.84 (ABq, 2, J = 18.0 Hz, C$_2$—H), 3.78 ($s$, 2, side chain CH$_2$), 4.90 ($d$, 1, J = 4.0 Hz, C$_6$—H), and 5.85 ppm ($q$, 1, J = 4.0 and 9.0 Hz, C$_7$—H).

EXAMPLE 25

7-(2-thienylacetamido)-3-cephem-3,4-dicarboxylic acid.

Cold trifluoroacetic acid (6 ml.) was added to a cooled solution of benzhydryl 7-(2-thienylacetamido)-3-benzhydryloxycarbonyl-3-cephem-4-carboxylate (0.710 g., 1.01 mmol.) in 6 ml. of anisole. The solution was stirred with cooling for ten minutes after which time was added 50 ml. of n-heptane. Evaporation in vacuo to low volume gave a precipitate which was filtered and dissolved in acetone. This solution was filtered, and the filtrate evaporated to dryness. The product was dissolved in cold ethyl acetate and extracted with cold sodium bicarbonate solution (2×). The aqueous extracts were combined, layered with cold ethyl acetate, and acidified with cold 1N.HCl. The ethyl acetate layer was separated, washed with brine, and dried ($Na_2SO_4$). Evaporation to dryness gave a crude product which was crystallized from ethyl formate to give 0.260 g. of 7-(2-thienylacetamido)-3-cephem-3,4-dicarboxylic acid as tan needles (mp 124.5°–125.5° C.); nmr (acetone-$d_6$) 3.40, 3.92 (AB$q$, 2, J = 18.0 Hz, $C_2$—H), 3.95 ($s$, 2, side chain $CH_2$), 5.20 ($d$, 1, J = 4.0 Hz, $C_6$—H), and 5.92 ppm ($q$, 1, J = 4.0 and 8.0 Hz, $C_7$—H).

EXAMPLE 26

Benzhydryl 7-(2-thienylacetamido)-3-ethylcarbonyldioxycarbonyl-2-cephem-4-carboxylate.

To a cooled (−10° C.), stirred solution of benzhydryl 7-(2-thienylacetamido)-3-carboxy-2-cephem-4-carboxylate (0.267 g., 0.5 mmol.) in 20 ml. methylene chloride under argon was added 0.051 g. triethylamine (0.5 mmol.). After stirring for several minutes at −10° C., the mixture was cooled to −20° and 0.162 g., (1.5 mmol.) ethyl chloroformate was added. The reaction mixture was allowed to stir at −20° for 30 minutes, and then allowed to warm to 0°. Cold ethyl acetate was added, and the resultant solution was washed successively with cold water, cold 1N.HCl, and cold brine and then dried ($Na_2SO_4$). Evaporation in vacuo to dryness gave 283 mg. (93.5%) of the mixed anhydride as a colorless froth. ir ($CHCl_3$) 1789 $cm^{-1}$ ($\beta$-lactam C = 0); nmr ($CDCl_3$) 1.34 ($t$, 3, J = 7.0 Hz, $CH_2CH_3$), 3.80 ($s$, 1, side chain $CH_2$), 4.30 ($q$, 2, J = 7.0 Hz, $CH_2CH_3$), 5.02 ($d$, 1, J = 4.0 Hz, $C_6$—H), 5.40 ($q$, 1, 4.0 and 8.0 Hz, $C_7$—H), 5.55 ($s$, 1, $C_4$—H), and 4.72 ppm ($s$, 1, $C_2$—H).

EXAMPLE 27

Benzhydryl 7-(2-thienylacetamido)-3-azidocarbonyl-2-cephem-4-carboxylate.

To a stirred solution of benzhydryl 7-(2-thienylacetamido)-3-ethylcarbonyldioxycarbonyl-2-cephem-4-carboxylate (0.283 g., 0.468 mmol.) in 20 ml. of tetrahydrofuran at room temperature was added 0.12 g. sodium azide (1.85 mmol.). The mixture was stirred at room temperature for 10 minutes and was then transferred to a separating funnel with the aid of ethyl acetate. The solution was washed with water and brine and subsequently dried ($Na_2SO_4$). Evaporation to dryness gave 265 mg. of the acyl azide as a brown froth: ir ($CHCl_3$) 2143 (C-$N_3$) and 1785 $cm^{-1}$ ($\beta$-lactam C = 0); nmr ($CDCl_3$) 3.77 ($s$, 2, side chain $CH_2$), 4.95 ($d$, 1, J = 4.0 Hz, $C_6$—H), 5.35 ($q$, 1, J = 4.0 and 8.0 Hz, $C_7$—H), 5.49 ($s$, 1, $C_4$—H), and 7.72 ppm ($s$, 1, $C_2$—H).

EXAMPLE 28

Benzhydryl 7-(2-thienylacetamido)-3-carbamyl-2-cephem-4-carboxylate.

A solution of benzhydryl 7-(2-thienylacetamido)-3-azidocarbonyl-2-cephem-4-carboxylate (0.253 g., 0.45 mmol.) in 2 ml. of methylene chloride and 50 ml. of methanol was combined with 0.267 g. of 5% Pd/C (prereduced at 50 psi/15 min.) in 30 ml. of 3A ethanol. Hydrogenation of the acyl azide was carried out at 50 psi for 3 hours at room temperature. The mixture was filtered, and the filtrate was evaporated to dryness. The product was dissolved in methylene chloride/acetone. The resultant solution was filtered through a Celite filter pad. The filtrate was evaporated in vacuo to dryness to give 0.179 g. (74.5%) of benzhydryl 7-(2thienylacetamido)-3-carbamyl-2-cephem-4-carboxylate as a white solid, identical to the product derived from the reaction of ammonia and the corresponding 3-carboxylic acid chloride.

EXAMPLE 29

Benzhydryl 7-(2-thienylacetamido)-3-(phenylthio)carbonyl-2-cephem-4-carboxylate.

To a cooled (−10° C.), stirred solution of benzhydryl 7-(2-thienylacetamido)-3-carboxy-2-cephem-4-carboxylate (.267 g., 0.5 mmol.) in 25 ml. of methylene chloride under an argon atmosphere was added 0.152 g. (1.5 mmol.) of N-methylmorpholine. The reaction mixture was then cooled to −20° C. and 0.135 g. (1.25 mmol.) of ethyl chloroformate was added. The mixture was stirred at 0° for 30 minutes after which time the mixture was cooled to −10° and 0.165 g. of thiophenol was added. After stirring the reaction mixture at 0° for 1 hour, ethyl acetate was added, and the resulting solution was washed successively with aqueous sodium bicarbonate, water, and brine and then dried over anhydrous sodium sulfate. Evaporation in vacuo to dryness gave a product which was chromatographed on a silica gel column using a tolueneethyl acetate gradient to provide 0.208 g. (66.5%) of the title product: ir ($CHCl_3$) 1798 $cm^{-1}$ ($\beta$-lactam C = 0); nmr ($CDCl_3$) 3.80 ($s$, 2, side chain $CH_2$), 5.06 ($d$, 1, J = 4.0 Hz, $C_6$—H), 5.42 ($q$, 1, J = 4.0 and 8.0 Hz, $C_7$—H), 5.70 ($s$, 1, $C_4$—H) and 7.87 ppm ($s$, 1, $C_2$—H).

EXAMPLE 30

Benzhydryl 7-(2-thienylacetamido)-3-(N,N-dimethylcarboxamido)-2-cephem-4-carboxylate.

To a cooled (5°), stirred solution of benzhydryl 7-(2-thienylacetamido)-3-carboxy-2-cephem-4-carboxylate sodium salt (0.724 g., 1.305 mmol.) in 40 ml. of methylene chloride plus two drops of dimethylformamide was added a solution of oxalyl chloride (0.430 g., 3.4 mmol.) in 3 ml. of methylene chloride. The mixture was allowed to stir with cooling for one hour, after which time the mixture was evaporated to dryness in vacuo at low temperature. The residue was dissolved in 25 ml. of methylene chloride and the mixture cooled to −73° C. To this solution was added a solution of dimethylamine (0.147 g., 3.26 mmol.) in 3 ml. of cold methylene chloride. The dark brown solution was stirred at −73° for 20 minutes, after which time was added 3 ml. of 1N.HCl. The reaction mixture was allowed to warm to 10° C., ethyl acetate was added, and the resulting solution was washed successively with 1N.HCl, sodium bicarbonate solution (2X), brine, and dried ($Na_2SO_4$). Evaporation in vacuo to dryness gave 0.883 g. of a brown solid which was recrystallized from acetone-hexane to provide 0.369 g. (51%) of benzhydryl 7-(2-thienylacetamido)-3-(N,N-dimethylcarboxamido)-2-cephem-4-carboxylate as tan flakes: nmr (DMSO-$d_6$) 2.70 (s, 6, N($CH_3$)$_2$), 3.75 (s, 2, side chain $CH_2$) 5.12 (d, 1, J = 4.0 Hz, $C_6$—H), and 5.52 ppm (m, 2, $C_7$—H and $C_4$—H).

Analysis Calcd. for $C_{29}H_{27}N_3O_5S_2$: C, 62.46; H, 4.16; N, 7.54; Found: C, 62.22; H, 4.37; N, 7.46.

EXAMPLE 31

Benzhydryl 7-(2-thienylacetamido)-3-(N,N-dimethylcarboxamido)-3-cephem-4-carboxylate.

The same oxidation-reduction procedure was followed as described in Example 3. The 3-cephem compound was isolated in 39.6% overall yield from the corresponding 2-cephem compound: ir $CHCl_3$) 1788 $cm^{-1}$ (β-lactam C = O); nmr ($CDCl_3$) 2.66 (s, 6, N($CH_3$)$_2$), 3.35, 3.67 (ABq, 2, J = 18.0 Hz, $C_2$—H), 3.84 (s, 2, side chain $CH_2$), 4.95 (d, 1, J = 4.0 Hz, $C_6$—H), and 5.86 ppm (q, 1, J = 4.0 and 8.0 Hz, $C_7$-H).

EXAMPLE 32

7-(2-thienylacetamido)-3-(N,N-dimethylcarboxamido)-3-cephem-4-carboxylic acid.

To a cooled (5° C.), stirred solution of benzhydryl 7-(2-thienylacetamido)-3-(N,N-dimethylcarboxamido)-3-cephem-4-carboxylate in 5 ml. of anisole was added 5 ml. of cold trifluoroacetic acid. The mixture was stirred with cooling for 10 minutes after which time 40 ml. of n-heptane was added. Evaporation in vacuo to a low volume gave a precipitate which was filtered and dissolved in acetone. The acetone solution was filtered and the filtrate evaporated to dryness. The product was dissolved in ethyl acetate and extracted with sodium bicarbonate solution. The aqueous extracts were combined, layered with cold ethyl acetate, annd acidified with 1N.HCl. The organic layer was separated, washed with brine and dried ($Na_2SO_4$). Evaporation in vacuo to dryness gave 24 mg. (21%) of the acid.

EXAMPLE 33

Benzhydryl 7-amino-3-(2-bromoethoxycarbonyl)-3-cephem-4-carboxylate.

Phosphorous pentachloride (0.186 g., benzhydryl mmol.) was added to a stirred slurry of benzhydryl 7-(2-thienylacetamido)-3-(2-bromoethoxycarbonyl)-3-cephem-4-carboxylate (0.500 g., 0.78 mmol.) and pyridine (0.078 ml., 0.962 mmol.) and 9 ml of methylene chloride. After stirring for two hours and ten minutes at room temperature, the reaction mixture was cooled briefly in a dry iceacetone bath, and isobutanol (0.39 ml., 4.20 mmol.) was added. The mixture was allowed to stir at ambient temperature for one hour. Addition of n-hexane resulted in the formation of a gum which was then taken up in a slurry of ethyl acetate and sodium bicarbonate solution. The ethyl acetate layer was separated, washed with sodium bicarbonate solution and brine and dried over sodium sulfate. Evaporation in vacuo to dryness gave 0.302 g. (75%) of benzhydryl 7-amino-3-(2-bromoethoxycarbonyl)-3-cephem-4-carboxylate as a brown froth (single spot on tlc).

EXAMPLE 34

Benzhydryl 7-[D-(2-phenyl-2-formyloxyacetamido)]-3-(2-bromoethoxycarbonyl)-3-cephem-4-carboxylate To a cooled (ice bath), stirred solution of benzhydryl 7-amino-3-(2-bromoethoxycarbonyl)-3-cephem-4-carboxylate (0.302 g., 0.58 mmol.) in 30 ml. of tetrahydrofuran was added sodium bicarbonate (0.043 g., 0.64 mmol.) and D-(2-phenyl-2-formyloxyacetic acid chloride (0.127 g., 0.64 mmol.). After allowing the mixture to stir 30 minutes with cooling, ethyl acetate was added, and the reaction mixture was then washed with water and brine and then dried over anhydrous sodium sulfate. Evaporation in vacuo to dryness gave a residue which was chromatographed on silica gel using a toluene-ethyl acetate gradient to give 0.194 g. (49%) of benzhydryl 7-[D-(2-phenyl-2-formyloxyacetamido)]-3-(2-bromoethoxycarbonyl)-3-cephem-4-carboxylate as a white solid which was crystallized from a methylene chloride-hexane mixture to give fine white needles (mp 196°-197°): nmr ($CDCl_3$) 3.13 (m, 2, $CH_2$—Br), 3.6 (center of ABq for $C_2$—H), 4.0 (m, 2, $CO_2CH_2$), 4.90 (d, 1, J = 5.0 Hz, $C_6$—H), 5.3 (q, 1, J = 5.0 and 9.0 Hz, $C_7$—H), 6.20 (s, 1, side chain CH), and 8.09 ppm (s, 1, CHO).

Analysis Calcd. for $C_{32}H_{27}BrN_2O_8S$: C, 56.56; H, 4.01; N, 4.12; Found: C, 56.57; H, 3.84; N, 3.99.

EXAMPLE 35

7-[D-(2-phenyl-2-formyloxyacetamido)]-3-(2-bromoethoxycarbonyl)-3-cephem-4-carboxylic acid.

To a cooled (ice bath) slurry of benzhydryl 7-[D-(2-phenyl-2-formyloxyacetamido)]-3-(2-bromoethoxycarbonyl)-3-cephem-4-carboxylate (0.160 g., 0.235 mmol.) in 1 ml. of anisole was added 1 ml. of cold trifluoroacetic acid. After stirring the mixture with cooling for ten minutes, 10 ml. of n-heptane was added. The mixture was evaporated in vacuo to low volume and 30 ml. of n-heptane was added. After stirring the reaction mixture in an ice bath for five minutes the mixture was filtered. The solid was dissolved in acetone, and the acetone solution was filtered. The filtrate was evaporated to dryness to give a residue which crystallized from acetone-hexane to give 100 mg. (83.6%) of 7-[D-(2-phenyl-2-formyloxyacetamido)]-3-(2-bromoethoxycarbonyl)-3-cephem-4-carboxylic acid as a white solid (mp 171°-172° C. decomp):

Analysis Calcd. for $C_{19}H_{17}BrN_2O_8S$: C, 44.46; H, 3.34; N, 5.46; Found: C, 44.69; H, 3.62; N, 5.54.

EXAMPLE 36

Benzhydryl 7-amino-3-methoxycarbonyl-3-cephem-4-carboxylate.

The same side chain cleavage procedure was followed as described in Example 33. The corresponding 2-thienylacetamido compound was used as a starting material. The product nucleus diester was isolated in 93% yield (single spot on tlc): ir ($CHCl_3$) 1795 $cm^{-1}$ (β-lactam C = O); nmr ($CDCl_3$) 1.84 (broad singlet, 2, $NH_2$, exchangeable with $D_2O$), 3.27 (s, 3, $CO_2CH_3$), 3.41, 3.90 (ABq, 2, J = 18.0 Hz, $C_2$—H), 4.70 (d, 1, J = 5.0 Hz, $C_6$—H), 4.92 (d, 1, J = 5.0 Hz, $C_7$—H), 7.11 (s, 1, benzhydryl CH) and 7.4 ppm (s, 10, benzhydryl ArH).

EXAMPLE 37

Benzhydryl 7-[D-(2-phenyl-2-formyloxyacetamido)]-3-methoxycarbonyl-3-cephem-4-carboxylate.

The same acylation procedure was followed as described in Example 34 except benzhydryl 7-amino-3-methoxycarbonyl-3-cephem-4-carboxylate was used as the starting material. Chromatography provided 0.211 g. (61.2%) of the product which crystallized from methylene chloride-hexane to give fine white needles (mp 207°–208°): ir ($CHCl_3$) 1800 cm$^{-1}$ ($\beta$-lactam C = 0); nmr (acetone $d_6$) 3.34 (s, 3, $CO_2CH_3$), 3.7 (m, $C_2$-H), 5.15 (d, 1, J = 5.0 Hz, $C_6$—H), 5.95 (q, J = 5.0 and 9.0 Hz, $C_7$—H), 6.30 (s, 1, side chain CH), 7.10 (s, 1, benzhydryl CH), 7.5 (m, 10, benzhydryl ArH), 8.34 (s, 1, CHO), and 8.43 ppm (d, 1, J = 9.0 Hz, NH).

Analysis Calcd. for $C_{31}H_{26}N_2O_8S$: C, 63.47; H, 4.47; N, 4.78; Found: C, 63.40; H, 4.73; N, 4.53.

EXAMPLE 38

7-[D-(2-phenyl-2-formyloxyacetamido)]-3-methoxycarbonyl-3-cephem-4-carboxylic acid.

The same procedure was followed as in Example 4 wherein the benzhydryl ester is deesterified by treatment with trifluoroacetic acid in anisole. The product was crystallized from acetone methylene chloride-hexane to provide white crystals (mp 177°–178°).

Analysis Calcd. for $C_{18}H_{16}N_2O_8S$: C, 51.43; H, 3.84; N, 6.66; Found: C, 51.70; H, 4.06; N, 6.77.

EXAMPLE 39

Benzhydryl 7-[(2,5-dichlorophenylthio)acetamido]-3-methoxycarbonyl-3-cephem-4-carboxylate.

To a cooled (5° C.), stirred solution of benzhydryl 7-amino-3-methoxycarbonyl-3-cephem-4-carboxylate (.268 g., 0.632 mmol.) in 30 ml. of tetrahydrofuran was added 0.239 g. (28.4 mmol.) sodium bicarbonate and 0.390 g. (1.52 mmol.) of (2,5-dichlorophenylthio)acetic acid chloride. The mixture was stirred with cooling for 1 hour. Ethyl acetate was added, and the resulting solution was washed with water and brine and then dried over anhydrous sodium sulfate. Chromatography on silica gel using a toluene-ethyl acetate gradient gave 0.288 g. (71%) of the title compound as a white solid which crystallized from methylene chloride-hexane to give 173 mg. of colorless crystals (mp 179°–180°): ir ($CHCl_3$) 1805 cm$^{-1}$; nmr ($CDCl_3$, acetone d-6) 3.30 (s, 3, $CO_2CH_3$), 3.50, 3.85 (ABq, 2, J = 16 Hz, $C_2$—H), 3.93 ( s, 2,

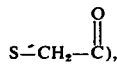

5.15 (d, 1, J = 4.0 Hz, $C_6$—H), and 5.85 ppm (q, 1, J = 4.0 and 8.0 Hz, $C_7$—H).

Analysis Calcd. for $C_{30}H_{24}N_2O_6S_2Cl_2$: C, 55.99; H, 3.76; N, 4.35; Found: C, 56.02; H, 3.79; N, 4.17

The corresponding acid, 7-[(2,5-dichlorophenylthio)acetamido]-3-methoxycarbonyl-3-cephem-4-carboxylic acid, is prepared by cleavage of the benzhydryl ester with trifluoroacetic acid and anisole as described above in Example 4. The product exhibited antimicrobial activity.

EXAMPLE 40

Benzhydryl 7-(2-phenyl-2-tert-butoxycarbonylacetamido)-3-methoxycarbonyl-3-cephem-4-carboxylate.

The same acylation procedure was followed as described in Example 34 except benzhydryl 7-amino-3-methoxycarbonyl-3-cephem-4-carboxylate was acylated using dl-2-(tert-butoxycarbonyl)-2-phenylacetyl chloride as the acylating agent. Chromatography of the reaction product provided the title diester (63.3%) which was crystallized from methylene chloride-hexane to give a white solid (mp 184°–185°): ir ($CHCl_3$) 1801 cm$^{-1}$ ($\beta$-lactam C = 0); nmr ($CDCl_3$) 1.47 (s, 9, tert-butyl), 3.27 (s, 3, $CO_2CH_3$), 3.40, 3.80 (ABq, 2, J = 18.0 Hz, $C_2$—H), 4.45, 4.50 (2-s, 1, side chain CH), 4.93, 4.96 (2-d, 1, J = 5.0 Hz, $C_6$—H), 5.87 (q, 1, J = 5.0 and 9.0 Hz, $C_7$—H), 7.10 (s, 1, $CH_2$), 7.4 (Ar), and 7.29, 8.15 ppm (2-d, 1, J = 9.0 Hz, NH).

Analysis Calcd. for $C_{35}H_{34}N_2O_8S$: C, 65.41; H, 5.33; N, 4.36; Found: C, 65.26; H, 5.55; N, 4.19.

EXAMPLE 41

7-(2-phenyl-2-carboxyacetamido)-3-methoxycarbonyl3-cephem-4-carboxylic acid disodium salt.

Benzhydryl 7-(2-phenyl-2-tert-butoxycarbonylacetamido)-3-methoxycarbonyl-3-cephem-4-carboxylate (0.257 g., 0.399 mmol.) was dissolved in 40 ml. 97-100% formic acid and allowed to react for 1 hour at room temperature. The reaction mixture was evaporated to dryness to give a residue which was dissolved in ethyl acetate and extracted with sodium bicarbonate solution. The aqueous extracts were combined, layered with cold ethyl acetate, and acidified with cold 1N.HCl. The organic layer was separated, washed with brine and dried ($Na_2SO_4$). Evaporation to dryness gave 0.209 g. of acid which was dissolved in 40 ml. ethanol and treated with 2 equivalents of sodium 2-ethylhexanoate. The solution was evaporated in vacuo until a precipitate was noted. The solution was placed in the refrigerator overnight and filtered to give 27 mg. of the disodium salt: nmr (acetone-$d_6$) 3.75 (m, 5, $CO_2CH_3$, $C_2$—H), 4.85 (2-s, 1, side chain CH), 5.17, 5.28 (2-d, 1, J = 5.0 Hz, $C_6$—H), and 5.92 ppm (q, 1, J = 5.0 Hz and 9.0 Hz, $C_7$—H).

Note: Doubling of some peaks is due to dl mixture.

EXAMPLE 42

Benzhydryl 7-D-[(2-phenyl-2-tert-butoxycarbonylamino)acetamido]-3-methoxycarbonyl-3-cephem-4-carboxylate.

To a cooled (−20° C.), stirred solution of N-t-butoxycarbonylphenylglycine (0.222 g., 0.882 mmol.) in 30 ml. tetrahydrofuran under argon was added N-methylmorpholine (0.089 g., 0.882 mmol.) following which was added methyl chloroformate (0.097 g., 1.03 mmol.). The mixture was allowed to react for 10 minutes at −20° C. after which time the mixture was cooled to −30°, and a solution of benzhydryl 7-amino-3-methoxycarbonyl-3-cephem-4-carboxylate (0.312 g., 0.735 mmol.) in 8 ml. tetrahydrofuran was added dropwise. The mixture was allowed to react at −25° to −5° for 30 minutes. Cold ethylacetate was added, and the mixture was then washed with cold 1N.HCl, cold sodium bicarbonate solution, and brine, and dried (Na$_2$SO$_4$). Evaporation and chromatography on silica gel using a toluene-ethyl acetate gradient provided 0.305 g. (63%) of the title product: ir (CHCl$_3$) 1800 cm$^{-1}$ (β-lactam C = 0); nmr (CDCl$_3$) 1.42 (s, 9, tert-butyl), 3.25 (s, 3, CO$_2$CH$_3$), 3.26, 3.75 (ABq, 2, J = 18.0 Hz, C$_2$—H), 4.85 (d, 1, J = 5.0 Hz), 5.32 (d, 1, J = 6.0 Hz, side chain CH and C$_6$—H), and 5.82 ppm (m, 2, C$_7$—H and NH).

When the amino ester was reacted with N-t-butoxycarbonylphenylglycine in the presence of a condensing agent (EEDQ) the above product was isolated in 42% yield.

EXAMPLE 43

7-D-(2-phenyl-2-aminoacetamido)-3-methoxycarbonyl-3-cephem-4-carboxylic acid.

Benzhydryl 7-D-[(2-phenyl-2-tert-butoxycarbonylamino) acetamido]-3-methoxycarbonyl-3-cephem-4-carboxylate (0.168 g., 0.256 mmol.) was dissolved in 95 ml. of 97–100% formic acid, and the mixture was stirred at room temperature for 30 minutes. Evaporation in vacuo to dryness gave a product which was insoluble in CDCl$_3$ and acetone-d$_6$. The material was dissolved in 3 ml. of cold trifluoroacetic acid. The mixture was stirred in an ice bath for 10 minutes, diluted with n-heptane and evaporated to dryness. The product was dissolved in acetonitrile (9 ml.), 1 ml. of water was added, and pH was adjusted to 4.5 with dilute sodium hydroxide. No precipitate formed. Freeze-drying gave a product which crystallized upon addition of 2 drops of water, 5 drops of acetonitrile, 4 drops of water and 4 ml. of acetonitrile repsectively.

EXAMPLE 44

Benzhydryl 7-amino-3-(4-nitrobenzyloxycarbonyl)-3-cephem-4-carboxylate.

Using the corresponding 7-thienylacetamido compound as starting material, the amide side chain was cleaved in accordance with the procedure described in Example 33. The product amino ester was isolated in 89% yield: ir (CDCl$_3$) 1799 cm$^{-1}$ (β-lactam C = 0); nmr (CDCl$_3$) 2.80 (broad singlet, NH$_2$), 3.74 (center of ABq for C$_2$—H), and 4.85 ppm (m, 4, C$_6$—H, C$_7$—H, annd ester CH$_2$).

EXAMPLE 45

Benzhydryl 7-[D-(2-phenyl-2-formyloxyacetamido)]-3-(4-nitrobenzyloxycarbonyl)-3-cephem-4-carboxylate.

To a cooled (5° C.), stirred solution of benzhydryl 7-amino-3-(4-nitrobenzyloxycarbonyl)-3-cephem-4-carboxylate (0.305 g., 0.559 mmol.) in 25 ml. tetrahydrofuran was added sodium bicarbonate (0.052 g., 0.615 mmol.) following which was added D-2-phenyl-2-formyloxyacetyl chloride (0.122 g., 0.615 mmol.). The mixture was allowed to react with cooling for 30 minutes. Ethyl acetate was added and the mixture then washed with cold water and brine and dried (Na$_2$SO$_4$). Evaporation to dryness and chromatography of the product on silica gel using a toluene-ethyl acetate gradient provided 0.183 g. (46.4%) of the acylated benzhydryl ester: ir (CHCl$_3$) 1802 Cm$^{-1}$ (β-lactam C = 0); nmr (CDCl$_3$) 3.37, 3.88 (ABq, 2, J = Hz, C$_2$—H), 4.67, 4.85 (ABq, 2, J = 14.0 Hz, p-nitrobenzyl CH$_2$), 4.88 (d, 1, J = 5.0 Hz, C$_6$—H), 5.75 (q, 1, J = 5.0 and 9.0 Hz, C$_7$—H), 6.18 (s, 1, side chain CH), and 8.05 ppm (s, 1, CHO).

EXAMPLE 46

7-[D-(2-phenyl-2-formyloxyacetamido)]-3-(4-nitrobenzyloxycarbonyl)-3-cephem-4-carboxylic acid.

The same procedure was followed as described in Example 4 wherein the benzhydryl group was removed by treatment with trifluoroacetic acid to give the corresponding acid. The product crystallized from acetone/hexane to give 0.081 g. (65%) of tan crystals (mp 154°–155°).

Analysis Calcd. for C$_{24}$H$_{19}$N$_3$O$_{10}$S: C, 53.24; H, 3.54; N, 7.76; Found: C, 53.28; H, 3.68; N, 7.47.

EXAMPLE 47

Benzhydryl 7-[D-(2-phenyl-2-formyloxyacetamido)]-3-carboxy-3-cephem-4-carboxylate.

Benzhydryl 7-[D-(2-phenyl-2-formyloxyacetamido)]-3-(4-nitrobenzyloxycarbonyl)-3-cephem-4-carboxylate (0.224 g., 0.3 mmol.) was dissolved in 5 ml. methylene chloride and 40 ml. methanol. Prereduced 5% Pd/C (.224 g.) was added to the solution. The hydrogenation was carried out at room temperature (hydrogen at 50 psi) for 2 hours. Filtration of the reaction mixture and evaporation of the filtrate to dryness gave the title product (190 mg.). The product exhibited antimicrobial activity against both gram-positive and gram-negative organisms.

I claim:
1. The compound of the formula

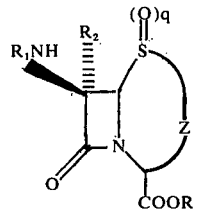

wherein Z is a group of the formula

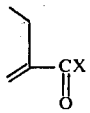

or

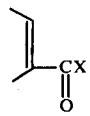

wherein X is a. azido, chloro, bromo, or C$_2$-C$_5$ alkylcarbonyldioxy; or
b. a group of the formula -OR$_3$ wherein R$_3$ is hydrogen, C$_1$-C$_6$ alkyl, C$_2$-C$_6$ haloalkyl, 2,2,2-trihaloethyl, methoxybenzyl, nitrobenzyl, benzyl, diphenylmethyl, C$_2$-C$_5$ alkanoyloxymethyl, phenyl or a pharmaceutically acceptable non-toxic cation; or c. a group of the formula —SR$_4$ wherein R$_4$ is C$_1$-C$_6$ alkyl, phenyl, benzyl, 1-methyl-1,2,3,4-tetrazol-5-yl or 1,3,4-thiadiazol-2-yl; or d. a group of the formula

wherein R$_5$ is hydrogen, C$_1$-C$_6$ alkyl, benzyl, phenyl, or tolyl and Q is hydrogen, C$_1$-C$_6$ alkyl, benzyl, C$_1$-C$_7$alkoxy, hydroxy, amino, anilino, guanyl, or C$_1$-C$_3$ acylamino with the limitation that when Q is guanyl or C$_1$-C$_3$ acylamino, R$_5$ is hydrogen; or wherein R$_5$, Q, and the nitrogen atom taken together form a 5 or 6 membered ring; and wherein R is hydrogen or a carboxylic acid protecting ester forming group; and when R is hydrogen, the pharmaceutically acceptable non-toxic salts of the acids represented thereby; and wherein R$_1$ is hydrogen or an acyl group of the formula

wherein R' is a. C$_1$-C$_7$ alkyl, C$_3$-C$_7$ alkenyl, cyanomethyl, halomethyl, 4-protected amino-4-protected carboxylbutyl; or b. the group -R'' wherein R'' is 1,4-cyclohexyldienyl, phenyl, or substituted phenyl wherein the substituents are 1–3 halogens, hydroxy, nitro, cyano, trifluoromethyl, C$_1$-C$_4$ alkyl, C$_1$-C$_4$ alkoxy, hydroxymethyl, or protected aminomethyl; or c. an arylalkyl group of the formula R''—(Y)$_m$—CH$_2$— wherein R'' is as defined above,
Y is O or S, and
m is 0 or 1; or d. a substituted arylalkyl group of the formula

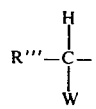

wherein R''' is R'' as defined above, 2-thienyl, or 3-thienyl; W is hydroxy or protected hydroxy, carboxy or protected carboxy, amino, protected amino; or e. a heteroarylmethyl group of the formula

R''''CH$_2$— wherein R'''' is 2-thienyl, 3-thienyl, 2-furyl, 3-furyl, 2-thiazolyl, 5-tetrazolyl or 1-tetrazolyl; and wherein R$_2$ is hydrogen or methoxy; and
q is 1 or 0 with the limitation that when q is 1, Z is

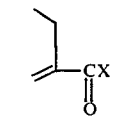

and R$_2$ is hydrogen.

2. The compound of claim 1 wherein R$_2$ is hydrogen.
3. The compound of claim 2 wherein q is 1.
4. The compound of claim 3 wherein R is p-nitrobenzyl, benzhydryl, p-methoxybenzyl, β,β,β-trichloroethyl, tert-butyl or β-iodoethyl.
5. The compound of claim 4 wherein R$_1$ is an acyl group of the formula

6. The compound of claim 5 wherein X is a group of the formula —OR$_3$.
7. The compound of claim 2 wherein q = 0.
8. The compound of claim 7 wherein Z is a group of the formula

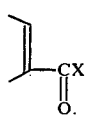

9. The compound of claim 8 wherein R is 4-nitrobenzyl, diphenylmethyl, 4-methoxybenzyl, 2,2,2-trichloroethyl, tert-butyl or 2-iodoethyl.
10. The compound of claim 9 wherein R$_1$ is an acyl group of the formula

11. The compound of claim 10 wherein X is a group of the formula —OR$_3$.
12. The compound of claim 11 wherein R$_3$ is C$_1$-C$_6$ alkyl or C$_2$-C$_6$ haloalkyl.
13. The compound of claim 11 wherein R$_3$ is hydrogen.
14. The compound of claim 10 wherein X is chloro, bromo, or C$_1$-C$_5$ alkylcarbonyldioxy.
15. The compound of claim 10 wherein X is azido.
16. The compound of claim 7 wherein Z is a group of the formula

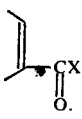

17. The compound of claim 16 wherein R is hydrogen, 4-nitrobenzyl, diphenylmethyl, 4-methoxybenzyl, 2,2,2-trichloroethyl, tert-butyl, iodoethyl, acetoxymethyl or pivaloyloxymethyl, and when R is hydrogen, the pharmaceutically acceptable non-toxic salts of the carboxylic acid represented thereby.
18. The compound of claim 17 wherein R$_1$ is an acyl group of the formula

19. The compound of claim 17 wherein $R_1$ is hydrogen, and X is a group of the formula —$OR_3$ or —$SR_4$.

20. The compound of claim 18 wherein X is a group of the formula —$OR_3$.

21. The compound of claim 20 wherein R is hydrogen and $R_3$ is hydrogen, $C_1$-$C_6$ alkyl or $C_2$-$C_6$ 2-haloalkyl.

22. The compound of claim 21 wherein R' is a substituted arylalkyl group of the formula

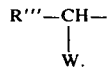

23. The compound of claim 22 said compound being 7-[D-(2-phenyl-2-formyloxyacetamido)]-3-methoxycarbonyl-3-cephem-4-carboxylic acid.

24. The compound of claim 22 said compound being 7-(2-phenyl-2-carboxyacetamido)-3-methoxycarbonyl-3-cephem-4-carboxylic acid.

25. The compound of claim 22 said compound being 7-[D-(2-phenyl-2-hydroxyacetamido)]-3-carboxy-3-cephem-4-carboxylic acid.

26. The compound of claim 18 wherein X is azido, chloro, bromo, or $C_2$-$C_5$ alkylcarbonyldioxy.

27. The compound of claim 18 wherein X is a group of the formula -$SR_4$.

28. The compound of claim 18 wherein X is a group of the formula

29. The compound of claim 19 wherein X is a group of the formula —$OR_3$.

30. The compound of claim 29 said compound being benzhydryl 7-amino-3-methoxycarbonyl-3-cephem-4-carboxylate.

31. The compound of claim 29 said compound being benzhydryl 7-amino-3-(2-bromoethoxycarbonyl)-3-cephem-4-carboxylate.

* * * * *

UNITED STATES PATENT AND TRADEMARK OFFICE
CERTIFICATE OF CORRECTION

PATENT NO. : 3,953,436
DATED : April 27, 1976
INVENTOR(S) : Douglas O. Spry

It is certified that error appears in the above-identified patent and that said Letters Patent are hereby corrected as shown below:

Column 4, line 7, "2-iodomethyl" should read --2-iodoethyl--.

Column 28, line 41, "chlorophenylaceamido" should read --chlorophenylacetamido--; line 68, "accmplished" should read --accomplished--.

Column 30, line 52, "cyclohexyloxycarabonyl" should read --cyclohexyloxycarbonyl--.

Column 32, line 16, "acaetone" should read --acetone--.

Column 36, line 61, "stitrred" should read --stirred--.

Column 40, line 66, "0 Hz" should read --6.0 Hz--.

Column 49, line 40, "1789" should read --1798--.

Column 51, line 45, "annd" should read --and--; line 55, "benzhydryl" should read --0.9--; line 56, "benzydryl" should read --benzhydryl--.

Column 55, line 49, "annd" should read --and--; line 68, "Cm$^{-1}$" should read --cm$^{-1}$--.

Column 56, line 1, "J=Hz" should read --J = 18.0 Hz--.

Column 59, line 7, "-or 3" should read -- -OR$_3$ --.

Signed and Sealed this

Fourth Day of January 1977

[SEAL]

Attest:

RUTH C. MASON
*Attesting Officer*

C. MARSHALL DANN
*Commissioner of Patents and Trademarks*